(12) United States Patent
Gillispie et al.

(10) Patent No.: US 6,896,880 B2
(45) Date of Patent: May 24, 2005

(54) METHOD FOR TREATING A DISEASE ASSOCIATED WITH EXCESSIVE OSTEOCLAST FORMATION

(75) Inventors: Matthew Todd Gillispie, Victoria (AU); Nicole Joy Horwood, Victoria (AU); Nobuyuki Udagawa, Chiba (JP); Masashi Kurimoto, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 6 days.

(21) Appl. No.: 10/100,057

(22) Filed: Mar. 19, 2002

(65) Prior Publication Data

US 2002/0150555 A1 Oct. 17, 2002

Related U.S. Application Data

(62) Division of application No. 09/030,061, filed on Feb. 25, 1998, now abandoned.

(30) Foreign Application Priority Data

Feb. 25, 1997 (JP) .............................................. 9-55468

(51) Int. Cl.⁷ .............................................. A61K 45/00
(52) U.S. Cl. ..................................... 424/85.2; 530/351
(58) Field of Search .......................... 424/85.2; 530/351

(56) References Cited

U.S. PATENT DOCUMENTS

| | | | |
|---|---|---|---|
| 4,588,585 A | 5/1986 | Mark et al. | |
| 5,776,731 A | 7/1998 | Parnet et al. | |
| 5,912,324 A | 6/1999 | Okamura et al. | |
| 6,156,301 A | 12/2000 | Namen et al. | |
| 6,207,641 B1 | 3/2001 | Torigoe et al. | ................ 514/12 |
| 6,476,197 B1 | 11/2002 | Yamamoto et al. | |

FOREIGN PATENT DOCUMENTS

| | | | |
|---|---|---|---|
| EP | 0 712 931 | 5/1996 | |
| EP | 0 712 931 A2 | 5/1996 | ........... C12N/15/19 |
| EP | 0 721 780 | 7/1996 | |
| EP | 0845530 | 6/1998 | |
| JP | 08-027189 | 1/1996 | |
| JP | 08-193098 | 7/1996 | |
| JP | 08-231598 | 9/1996 | |
| JP | 09-289896 | 11/1997 | |
| WO | 9744468 | 11/1997 | |

OTHER PUBLICATIONS

Merck Manual, 17th ed., "Hypercalcemia", p. 145–147.*
Dorland's Illustrated Medical Dictionary, 29th ed., W.B. Saunders Company, p. 1750.*
Dinarello et al. Overview of IL–18: more than an interferon–g inducing factor. J. Leukocyte Biology, 1998, 63:658–664.*
Kohno et al. Molecule of the month, IL–18, a cytokine which resembles IL–1 structurally and IL–12 functionally but exerts its effect independently of both. Clin. Immuno. Immunopath., 1998, 86: 11–15.*
Udagawa et al. IL–18 is produced by osteoblasts and acts via granulocyte/macrophage colony–stimulating factor and not via interferon–g to inhibit osteoclast formation. J. Exp. Med., Mar. 1997, 185:1005–1012.*
Martin et al., *Crit. Rev. Eukaryot. Gene Express* 812:107 (1998) (Abstract).
Udagawa et al., *J. Exp. Med.*, 185(6)1005–1012 (1998).
XP 002038817, Beier et al.
Martin et al., *Crit. Rev. Eukaryot. Gene Express*, 8(2)107 (1998) Abstract.
Udagaua et al., *J. Exp. Med.*, 185(6)1005–12 (1997).
Horwood et al., et al., *J. Clin. Invest.*, 585 (1998).
Henco, K. et al., "Structural relationship of human interferon alpha genes and pseudogenes.", *J.Mol.Biol.*, vol. 185, pp. 227–260 (1985).
Udagawa, N. et al., "Interleukin (IL)–6 induction of osteoclast differentiation depends on IL–6 receptors expressed on osteoblastic cells but not on osteoclast progenitors.", *J. Exp.Med.*, pp. 1461–1468 (1995).
Martin, T.J. et al., "Mechanisms by which cells of the osteoblast lineage control osteoclast formation and activity.", *J.Cell.Biochem.*, vol. 56, pp 357–366 (1994).
Ushio, S. et al., "Cloning of the cDNA for human IFN–gamma–inducing factor, expression in *Escherichia coli*, and studies on the biologic activities of the protein.", *J.Immuno.*, vol. 96, pp. 4274–4279 (1996).
Okamura, H. et al., "Cloning of a new cytokine that induces IFN–gamma production by T cells.", *Letters to Nature*, vol. 378, pp. 88–91 (1995).
Laemmli, U.K., "Cleavage of structural proteins during the assembly of the head of bacteriophage T4.", *Nature*, vol. 227, pp. 680–683 (1970).
Roodman, G., "Advances in bone biology: the osteoclast", *Endocrine Reviews*, vol. 17, pp. 308–332 (1996).
Excerpt Translation of: *Nikkei Biotechnology Report* 1996, pp. 498–499 (1995).

* cited by examiner

*Primary Examiner*—Lorraine Spector
*Assistant Examiner*—Dong Jiang
(74) *Attorney, Agent, or Firm*—Browdy and Neimark, PLLC

(57) ABSTRACT

An osteoclastgenic inhibitory agent which comprises an interleukin-18 and/or its functional equivalent. The agent can be arbitrarily used as an ingredient for cell culture and agents for regulating bone resorption and for osteoclast-related diseases, directed to treat and/or prevent hypercalcemia, osteoclastoma, osteoporosis, etc.

5 Claims, 3 Drawing Sheets

METHOD FOR TREATING A DISEASE ASSOCIATED WITH EXCESSIVE OSTEOCLAST FORMATION

CROSS-REFERENCE TO RELATED APPLICATIONS

This is a divisional of application Ser. No. 09/030,061, filed Feb. 25, 1998, now abandoned, the entire contents of which is incorporated herein by reference.

BACKGROUND OF THE INVENTION

1. Field of the Invention

The present invention relates to an osteoclastgenic inhibitory agent comprising an interleukin-18 (hereinafter abbreviated as "IL-18") or its functional equivalent.

2. Description of the Prior Art

Osteoblasts' bone formation and osteoclasts' bone resorption are well balanced in healthy living bodies, and this keeps the bone tissues in normal conditions while old bone tissues are being replaced with fresh ones without altering the original bone shape. The phenomenon plays an important role in keeping living bodies' homeostasis such as the controlling of blood calcium concentration within a desired range. Once the balance is lost, especially when the bone resorption level exceeds the bone formation level, bone-related diseases and other diseases may be induced. Therefore, elucidation of the whole mechanism of bone resorption in living bodies, particularly, elucidation of osteoclasts is greatly highlighted due to scientific and clinical significance thereof.

However, the mechanism of osteoclast formation has not yet been completely elucidated even though interleukin 1 as a promoter and interleukin 4 as an inhibitor were found. This is because, similarly as various phenomena in living bodies, osteoclast formation in living bodies is controlled by the close and complicated relationship between promoters and inhibitors. Based on these, it is greatly expected to establish an effective osteoclastgenic inhibitory agent from the viewpoint of scientific and clinical aspects.

SUMMARY OF THE INVENTION

The object of the present invention is to provide a novel and effective osteoclastgenic inhibitory agent. To solve the object the present inventors energetically studied for IL-18, i.e., one of cytokines as communication transferring substances in immune systems, which induces production of interferon-γ (hereinafter abbreviated as "IFN-γ"), an important biologically active substance for immunocompetent cells, and granulocyte/macrophage colony-stimulating factor (hereinafter abbreviated as "GM-CSF"), and augments cytotoxicity and induces formation of killer cells. At the finding, IL-18 was described as an interferon-γ-inducing factor as reported by Haruki OKAMURA in Japanese Patent Kokai Nos. 27,189/96 and 193,098/96, and in *Nature,* Vol. 378, No. 6,552, pp. 88–91 (1995), and then called IL-18 according to the proposal of Shimpei USHIO et al., in *The Journal of Immunology,* Vol. 156, pp. 4,274–4,279 (1996).

The present inventors found that a particular gene, capable of inhibiting osteoclast formation from osteoclastic precursor cells in vitro, is specifically expressed in quantities in stroma cells derived from mouse myeloma. Their further detailed analysis revealed that (i) the gene encodes IL-18 that includes SEQ ID NO: 7 as a core sequence, (ii) IL-18 and functional equivalents thereof effectively inhibit osteoclast formation, and (iii) the inhibition is mainly due to the action of GM-CSF induced and produced by IL-18.

Based on these, the present inventors solved the present object by an osteoclastgenic inhibitory agent comprising IL-18 or its functional equivalent as an effective ingredient.

BRIEF DESCRIPTION OF THE ACCOMPANYING DRAWINGS

Figure 1:
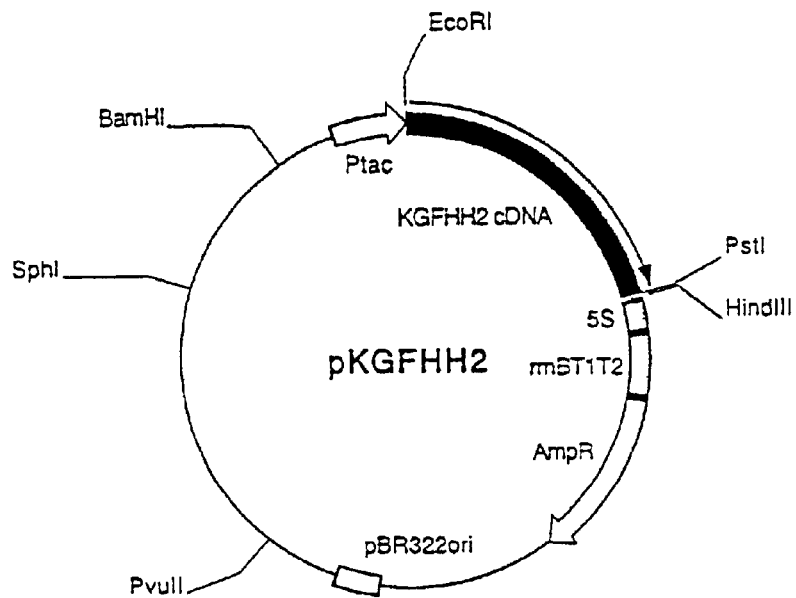
FIG. 1 shows the structure of the recombinant DNA pKGFHH2.

In these figures, KGFHH2 cDNA means a cDNA encoding the IL-18 according to the present invention: IGIF/MUT35; a DNA encoding the IL-18 according to the present invention: IGIF/MUT42; a DNA encoding the IL-18 according to the present invention: HuIGIF; a chromosomal DNA encoding the IL-18 according to the present invention: KGFMH2 cDNA; a cDNA encoding the IL-18 according to the present invention: 5S; a gene for 5S ribosomal RNA: Ptac; a tac promoter: rrnBTlT2; a termination region of a ribosomal RNA operon: AmpR; an ampicillin resistent gene: pBR322ori; a replication origin of *Escherichia coli:* CMV; a cytomegalovirus promoter: IFNss; a nucleotide sequence encoding a signal peptide for subtype a2b of human interferon-α.

DETAILED DESCRIPTION OF THE INVENTION

The present invention relates to an osteoclastgenic inhibitory agent comprising IL-18 or its functional equivalent as an effective ingredient. The wording "IL-18" as referred to in the invention includes polypeptides with the above property independently of their sources and origins. For example, the IL-18 used in the present invention includes, as internal partial amino acid sequences, the amino acid sequences of SEQ ID NO: 1, SEQ ID NO: 2, and SEQ ID NO: 3, as well as SEQ ID NO: 4 and SEQ ID NO: 5, and includes the amino acid sequence of SEQ ID NO: 6 or SEQ ID NO: 7 as a whole. The wording "functional equivalent(s)" as referred to in the present invention includes (i) those wherein one or more amino acids in the amino acid sequence of IL-18 are replaced with different amino acids, (ii) those wherein one or more amino acids are added to the N- and/or C-termini of the amino acid sequence of IL-18, (iii) those wherein one or more amino acids are inserted into the internal sites of the amino acid sequence of IL-18, (iv) those wherein one or more amino acids in the N- and/or C-terminal regions of the amino acid sequence of IL-18 are deleted, and (v) those wherein one or more amino acids in the internal regions of the amino acid sequence of IL-18 are deleted; all of these modifications should be made within the range that does not substantially lose the property of osteoclast formation by IL-18 among the inherent property of IL-18. Examples of such functional equivalents are described along with their detailed amino acid sequences in Japanese Patent Application No. 20,906/97 by the same applicant of the present applicant, i.e., polypeptides which are capable of inducing production of interferon-gamma by immunocompetent cells, wherein said polypeptides contain either amino acid sequence wherein one or more cysteines are replaced with different amino acid(s) while leaving respective consensus sequences as shown in SEQ ID NOs: 1, 2 and 4 intact, or that wherein one or more amino acids are added, removed and/or replaced at one or more sites including those in the consensus sequences but excluding those of the replaced cysteine. The different amino acids to replace the cysteine(s) are not restricted to any types, as far as the resulting polypeptide, containing an amino acid sequence replaced with the different amino acid(s), exhibits an activity of inducing production of IFN-γ by immunocompetent cells in the presence or absence of an appropriate cofactor, as the wild-type polypeptides containing SEQ ID NOs: 1, 2 and 4 as consensus partial amino acid sequences, and a stability significantly higher than that of the wild-type polypeptides. The different amino acids include serine, threonine, alanine, valine, leucine, isoleucine, histidine, tyrosine, phenylalanine, tryptophan, and methionine, among which the most preferable amino acid is serine or alanine. Embodiments of the amino acid sequences, containing SEQ ID NOs: 1, 2 and 4 as consensus partial amino acid sequences, in which one or more cysteines are to be replaced with different amino acid(s) are the wild-type polypeptides containing SEQ ID NO: 6 or 7. SEQ ID NO: 6 contains cysteines at the 38th, 68th, 76th, and 127th positions from the N-terminus. SEQ ID NO: 7 contains cysteines at the 7th, 75th, and 125th positions. The polypeptides include those containing the amino acid sequence of any one of SEQ ID NOs: 20–26, which are derived from the wild-type polypeptide containing SEQ ID NO: 6, those containing the amino acid sequence of SEQ ID NO: 27 or 28, which are derived from the wild-type polypeptide containing the amino acid sequence of SEQ ID NO: 7, and those containing an amino acid sequence derived from any one of SEQ ID NOs: 20–28 by adding, removing, and/or replacing one or more amino acids to and/or at position(s) excepting the positions where the cysteine(s) have been replaced while retaining the desired biological activities and stability. The wording "one or more amino acids" means the number of amino acids which conventional methods such as site-directed mutagenesis can usually add, remove or replace. The polypeptides containing any one of SEQ ID NOs: 20–28 possess both stability and biological activities significantly higher than those of the wild-type polypeptides.

The functional equivalents as referred to in the present invention further include glycosylated polypeptides of IL-18 and the above polypeptides. Any of these IL-18 and functional equivalents thereof, both of which are included to and referred to as "IL-18" in the present invention, unless specified otherwise, can be used in the present invention independently of their origins; those prepared by separating from natural sources such as cell cultures and from artificially synthesized ones using recombinant DNA technology and peptide synthesis.

With economical viewpoint, methods of recombinant DNA technology are advantageously used; generally, desired IL-18 can be obtained by introducing DNAs encoding IL-18 into appropriate hosts derived from microorganisms, plants, and animals to form transformants, culturing the transformants in nutrient culture media in a conventional manner, and purifying the cultures by conventional methods used for purifying cytokines. Any DNAs can be used as the above DNAs as long as they contain a DNA encoding IL-18, and can be suitably selected depending on the purpose of the use of the present osteoclastgenic inhibitory agent or on the recombinant DNA technology used. For example, Japanese Patent Kokai Nos. 193,098/96, 231,598/96, and 27,189/96 by the same applicant of the present invention disclose in detail methods for producing IL-18 by culturing transformed microorganisms into which DNAs including a cDNA encoding mouse or human IL-18 are introduced; and Japanese Patent Application No. 185,305/96 by the same applicant of the present invention discloses in detail a method for producing IL-18 encoding human IL-18 by culturing transformed animal cells which have an introduced DNA that includes a chromosomal DNA encodes human IL-18. Japanese Patent Application No. 20,906/97 by the same applicant of the present invention discloses in detail a method for producing IL-18 by culturing transformed animal cells having an introduced DNA which includes a DNA encoding a functional equivalent of human IL-18.

The aforesaid recombinant DNA technology has an economical advantage, but depending on the hosts and DNA sequences used, the IL-18 thus obtained may have somewhat different physicochemical property from those of IL-18 produced and functions in vivo. Japanese Patent Application No. 67,434/96 by the same applicant of the present invention discloses in detail a preparation of IL-18 using established human cell lines as natural sources, and Japanese Patent Application No. 213,267/96 by the same applicant also discloses in detail the preparation using an interleukin-1β-converting enzyme. The IL-18 obtained by those preparations can be estimated to have substantially the same or equal physicochemical property to that of IL-18 that is produced and functions in vivo, and the yield can be estimated to be slightly lower. However, such IL-18 has an advantage that it has a fewer side effects when used as pharmaceuticals directed to administering to warm-blooded animals in general and including humans. When applying purification methods using monoclonal antibodies specific to IL-18, as disclosed in Japanese Patent Application No. 231,598/96 by the same applicant of the present invention, a relatively-high purity IL-18 can be obtained in a minimum labor and cost.

The present osteoclastgenic inhibitory agent comprising the aforesaid IL-18 includes any types and forms usable to inhibit osteoclast formation both in vivo and in vitro. The present agent can be advantageously used as ingredients for cell culture media for animal cells, which satisfactorily inhibit osteoclast formation, maintain, proliferate, and/or differentiate the desired cells; components of screening kits for bone-related therapeutic agents; bone-resorption regulatory agents; and agents for osteoclast-related diseases. The bone-resorption regulatory agents include medicaments and health foods that exert an osteoclastgenic inhibitory activity in vivo, control bone resorption to normal conditions, and improve unfavorable physical conditions such as a relatively-insignificant arthralgia. The agents for osteoclast-related diseases include medicaments used to prevent and/or treat diseases caused by an excessive osteoclast formation and/or its function. Examples of such diseases are hypercalcemia, osteoclastoma, Behcet's syndrome, osteosarcoma, arthropathy, chronic rheumatoid arthritis, deformity ostitis, primary hyperthyroidism, osteopenia, and osteoporosis. Varying depending on the types of agents and diseases to be treated, the present agent is usually formulated into a liquid, paste, or solid form which contains 0.000002–100 w/w %, preferably, 0.0002–0.5 w/w % of IL-18.

The present osteoclastgenic inhibitory agent can be IL-18 alone or compositions comprising IL-18 and one or more other ingredients such as carriers, excipients, diluents, adjuvants, antibiotics, and proteins such as serum albumin and gelatin as stabilizers; saccharides such as glucose, maltose, maltotriose, maltotetraose, trehalose, sucrose, isomaltose, lactose, panose, erlose, palatinose, lactosucrose, raffinose, fructooligosaccharide, galactooligosaccharide, lentinan, dextrin, pullulan, and sugar alcohols including sorbitol, maltitol, lactitol, and maltotriitol; buffers comprising phosphates or citrates mainly; and reductants such as 2-mercaptoethanol, dithiothreitol, and reduced glutathione; and optionally biologically active substances such as interferon-α, interferon-β, interferon-γ, interleukin-2, interleukin-3, interleukin-6, interleukin-12, TNF-α, TNF-β, GM-CSF, estrogen, progesterone, chlormadinone acetate, calcitonin, somatokine, somatomedin, insulin-like growth factor, ipriflavone, parathyroid hormone (PTH), norethisterone, busulfan, ancitabine, cytarabine, fluorouracil, tetrahydrofurfuryl fluorouracil, methotrexate, vitamin $D_2$, active vitamin D, Krestin® or polysaccharide K, L-asparaginase, and OK-432 or Picibanil®; and calcium salts such as calcium lactate, calcium chloride, calcium monohydrogenphosphate, and L-calcium L-aspartate. When used as agents for administering to warm-blooded animals in general and including humans, i.e., agents for osteoclast-related diseases, the present agent can be preferably formulated into compositions by appropriately combining with one or more of the above physiologically-acceptable substances.

The present osteoclastgenic inhibitory agent includes medicaments in a unit dose form used for administering to warm-blooded animals in general and including humans. The wording "unit dose form" means those which contain IL-18 in an amount suitable for a daily dose or in an amount up to four fold by integers or up to 1/40 fold of the dose, and those in a physically separated and formulated form suitable for prescribed administrations. Examples of such formulations are injections, liquids, powders, granules, tablets, capsules, troches, collyriums, nebulas, and suppositories.

The present agent as an osteoclastgenic inhibitory agent effectively treat and prevent osteoclast-related diseases independently of oral and parenteral administrations. Varying depending on the types and symptoms of patients' diseases, the present agent can be administered to the patients orally, intradermally, subcutaneously, muscularly, or intravenously at a dose of about 0.5 µg to 100 mg per shot, preferably, at a dose of about 2 µg to 10 mg per shot of IL-18, 2–6 fold a day or 2–10 fold a week for one day to one year.

In the below, with reference to experiments, the preparation, physicochemical property, and biological activity of the IL-18 according to the present invention are described:

Experiment 1
Preparation of Human IL-18

According to the method in Japanese Patent Kokai No. 231,598/96 by the same applicant of the present invention, an autonomously-replicable recombinant DNA, pKGFHH2, linked to a cDNA encoding human IL-18, was prepared. Dideoxyribonucleotide sequencing analyzed that, as shown in FIG. 1, in the recombinant DNA, KGFHH2 cDNA containing the base sequence of SEQ ID NO: 8 was linked to the downstream of Ptac, a Tac promoter. The recombinant DNA pKGFHH2 contained the amino acid sequences of SEQ ID NOs: 1 to 5; these amino acid sequences were respectively encoded by nucleotides 46–63, 88–105, 400–420, 151–165, and 214–228 in SEQ ID NO: 8.

According to the method in Japanese Patent Kokai No. 231,598/96, the recombinant DNA pKGFHH2 was introduced into an *Escherichia coli* Y1090 strain, ATCC 37197, and the strain was cultured. The produced polypeptide was purified by immunoaffinity chromatography to obtain a purified human IL-18 with a purity of at least 95% in a yield of about 25 mg/l culture. According to the method in Japanese Patent Kokai No. 193,098/96 by the same applicant of the present invention, the purified human IL-18 was analyzed for biological activity and physicochemical property as indicated below: When culturing human lymphocytes, collected by a conventional manner from a healthy donor, in the presence of the purified human IL-18, IFN-γ production was observed depending on the concentration of IL-18, resulting in a confirmation that IL-18 has an activity of inducing IFN-γ production by lymphocytes as an immunocompetent cell. In accordance with the method as reported by U. K. Laemmli in *Nature*, Vol. 227, pp. 680–685 (1970), the purified IL-18 was subjected to SDS-PAGE, resulting in a major band with an IFN-γ inducing activity at a position corresponding to 18,500±3,000 daltons. The IL-18 gave a pI of 4.9±1.0 as determined by conventional chromatofocusing. Conventional analysis using "PROTEIN SEQUENCER MODEL 473A", an apparatus of Applied Biosystems, Inc., Foster City, USA, revealed that the IL-18 had the amino acid sequence of SEQ ID NO: 9, i.e., the amino acid sequence of SEQ ID NO: 8 where a methionine residue was linked to the N-terminus.

Experiment 2
Preparation of Human IL-18

According to the method in Japanese Patent Application No. 67,434/96 by the same applicant of the present invention, THP-1 cells, ATCC TIB 202, a human monocyte cell line derived from a male with acute monocytic leukemia, were inoculated to the dorsum subcutaneous tissues of new born hamsters, followed by feeding the hamsters for three weeks. Tumor masses, about 15 g weight each, formed in the subcutaneous tissues of each hamster, were extracted, dispersed in media, and disrupted. The polypeptide obtained from the disrupted cells was purified by immunoaffinity chromatography to obtain a purified human IL-18 in a yield of an about 50 ng/head.

Similarly, according to the method in Japanese Patent Application No. 67,434/96, the purified human IL-18 was analyzed and determined for biological activity and physicochemical property as indicated below: It was confirmed that culturing human lymphocytes, collected from healthy donors in a conventional manner, in the presence of different concentrations of the human IL-18, resulted in an IL-18 dose-dependent IFN-γ production. This revealed that the human IL-18 has a biological activity of inducing IFN-γ production by lymphocytes as an immunocompetent cell. In accordance with the method as reported by U. K. Laemmli in *Nature*, Vol. 227, pp. 680–685 (1970), the purified human IL-18 was subjected to SDS-PAGE using 2 w/v % dithiothreitol as a reductant, resulting in a major band with an IFN-γ production inducing activity at a position corresponding to 18,000–19,500 daltons. According to the peptide map disclosed in Japanese Patent Application No. 67,434/96, the human IL-18 was treated with clostripain commercialized by Sigma Chemical Company, Missouri, USA, to obtain polypeptide fragments, followed by subjecting the fragments for fractionation to high-performance liquid chromatography (HPLC) using "ODS-120T", a column commercialized by Tosoh Corporation, Tokyo, Japan, and analyzing the amino acid sequences of the fragments from the N-terminus to reveal the following amino acid sequences of SEQ ID NOs: 10 to 13. These amino acid sequences were completely coincided with amino acids 148–157, 1–13, 45–58, and 80–96 in SEQ ID NO: 6. The data shows that the human IL-18 obtained in Experiment 2 has the amino acid sequence of SEQ ID NO: 6 and all the partial amino acid sequences of SEQ ID NOs: 1 to 5.

Experiment 3
Preparation of Functional Equivalents

Figure 2:
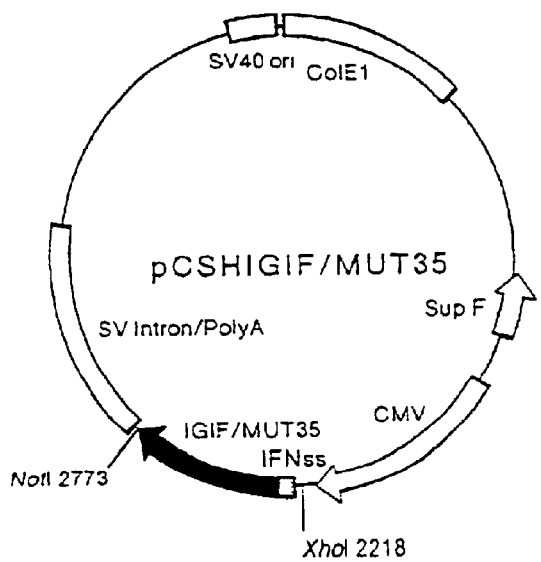
FIG. 2 shows the structure of the recombinant DNA pCSHIGIF/MUT35.

According to the method in Japanese Patent Application No. 20,906/97 by the same applicant of the present invention, it was prepared an autonomously-replicable recombinant DNA, pCSHIGIF/MUT35, was linked to a DNA encoding a functional equivalent of human IL-18 where cysteines 38, 68, and 76 in SEQ ID NO: 6 were respectively replaced with serine, serine, and alanine. Dideoxyribonucleotide sequence analysis revealed that as shown in FIG. 2, in the recombinant DNA, DNA IGIF/MUT35 with SEQ ID NO: 14 linked to the downstream of a base sequence encoding a signal peptide of subtype α2b in human interferon-α in the same reading-frame, as reported by K. Henco et al., in Journal of Molecular Biology, Vol. 185, pp. 227–260 (1985), and had a stop codon for protein synthesis at further downstream. As shown in parallel in SEQ ID NO: 14, the amino acid sequence encoded by the recombinant DNA corresponded to SEQ ID NO: 6 where cysteines 38, 68, and 76 in SEQ ID NO: 6 were respectively replaced with serine, serine, and alanine. The recombinant DNA contained a nucleotide which encodes all the amino acid sequences of SEQ ID NOs: 1 to 4 and the one of SEQ ID NO: 5 where cysteine at amino acid 5 in SEQ ID NO: 5 was replaced with alanine. These amino acid sequences were respectively encoded by nucleotides 46–63, 88–105, 400–420, 151–165, and 214–228 in SEQ ID NO: 14.

According to the method in Japanese Patent Application No. 20,906/97 by the same applicant of the present invention, the recombinant DNA pCSHIGIF/MUT35 was introduced into COS-1 cells, ATCC CRL 1650, an established cell line derived from SV40 transformed African Green monkey kidney, followed by culturing the transformed cells. The produced polypeptide in the culture was purified by immunoaffinity chromatography to obtain a purified functional equivalent of human IL-18 in a yield of about 40 ng/ml culture. According to the method in Japanese Patent Application No. 20,906/97, the purified functional equivalent was analyzed and determined for biological activity and physicochemical property as indicated below: When culturing KG-1 cells, ATCC CCL 246, an established cell line derived from human acute myelogenous leukemia, in the presence of different concentrations of the purified functional equivalent of human IL-18, IFN-γ. production was observed depending on the concentration of the IL-18, revealing that the IL-18 has a biological activity of inducing IFN-γ production by KG-1 cells as an immunocompetent cell. In accordance with the method as reported by U. K. Laemmli in Nature, Vol. 227, pp. 680–685 (1970), the purified functional equivalent was subjected to SDS-PAGE in the presence of 2 w/v % dithiothreitol as a reductant, resulting in a major band with an IFN-γ production inducing activity at a position corresponding to 18,000–19,500 daltons. Conventional analysis using "PROTEIN SEQUENCER MODEL 473A", an apparatus of Applied Biosystems, Inc., Foster City, USA, revealed that the N-terminal region of the functional equivalent had the amino acid sequence of SEQ ID NO: 15 which corresponded to the amino acid sequence in the N-terminal region as shown in parallel in SEQ ID NO: 14.

Experiment 4
Preparation of Functional Equivalent

Figure 3:
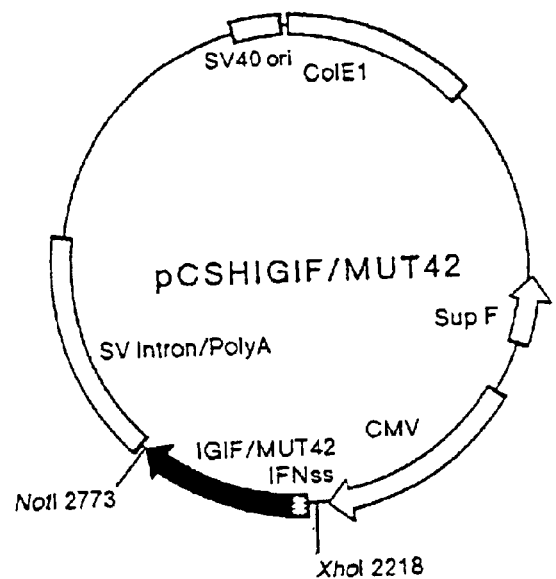
FIG. 3 shows the structure of the recombinant DNA pCSHIGIF/MUT42.

According to the method in Japanese Patent Application No. 20,906/97 by the same applicant of the present invention, it was prepared an autonomously-replicable recombinant DNA, pCSHIGIF/MUT42, which was linked to a DNA encoding for a functional equivalent of human IL-18 where cysteines 38, 68, 76, and 127 in SEQ ID NO: 6 were respectively replaced with serine, serine, alanine, and serine. Dideoxyribdnucleotide sequencing revealed that, as shown in FIG. 3, in the recombinant DNA, DNA IGIF/MUT42 with SEQ ID NO: 16 linked to the downstream of a base sequence encoding a signal peptide for subtype a2b of human interferon-α in the same reading frame, as reported by K. Henco et al., in Journal of Molecular Biology, Vol. 185, pp. 227–260 (1985), and had a stop codon for protein synthesis at further downstream. As shown in parallel in SEQ ID NO: 16, the amino acid sequence encoded by the recombinant DNA corresponded to SEQ ID NO: 6 where cysteines 38, 68, 76, and 127 in SEQ ID NO: 6 were respectively replaced with serine, serine, alanine, and serine. The recombinant DNA contained a nucleotide sequence which encodes all the amino acid sequences of SEQ ID NOs: 1 to 4 and the one of SEQ ID NO: 5 where cysteine 5 in SEQ ID NO: 5 was replaced with alanine. These amino acid sequences were respectively encoded by nucleotides 46–63, 88–105, 400–420, 151–165, and 214–228 in SEQ ID NO: 16.

According to the method in Japanese Patent Application No. 20,906/97 by the same applicant of the present invention, the recombinant DNA pCSHIGIF/MUT42 was introduced into COS-1 cells, followed by culturing the cells. The produced polypeptide in the culture was purified by immunoaffinity chromatography to obtain a purified functional equivalent of human IL-18 in a yield of about 20 ng/ml culture. According to the method in Japanese Patent Application No. 20,906/97, the purified functional equivalent was analyzed and determined for biological activity and physicochemical property as indicated below: When cultured KG-1 cells in the presence of different concentrations of the purified functional equivalent, a dose-dependent IFN-γ production was observed, and this revealed that the functional equivalent has a biological activity of inducing IFN-γ production by KG-1 cells as an immunocompetent cell. In accordance with the method as reported by U. K. Laemmli in Nature, Vol. 227, pp. 680–685 (1970), the purified functional equivalent was subjected to SDS-PAGE in the presence of 2 w/v % dithiothreitol as a reductant, resulting in a major band with an IFN-γ inducing activity at a position corresponding to 18,000–19,500 daltons. Conventional analysis using "PROTEIN SEQUENCER MODEL 473A", an apparatus of Applied Biosystems, Inc., Foster City, USA, revealed that the N-terminal region of the functional equivalent had the amino acid sequence of SEQ ID NO: 15 which completely corresponded to the amino acid sequence in the N-terminal region as shown in parallel in SEQ ID NO: 16.

Experiment 5
Preparation of Human IL-18

Figure 4:
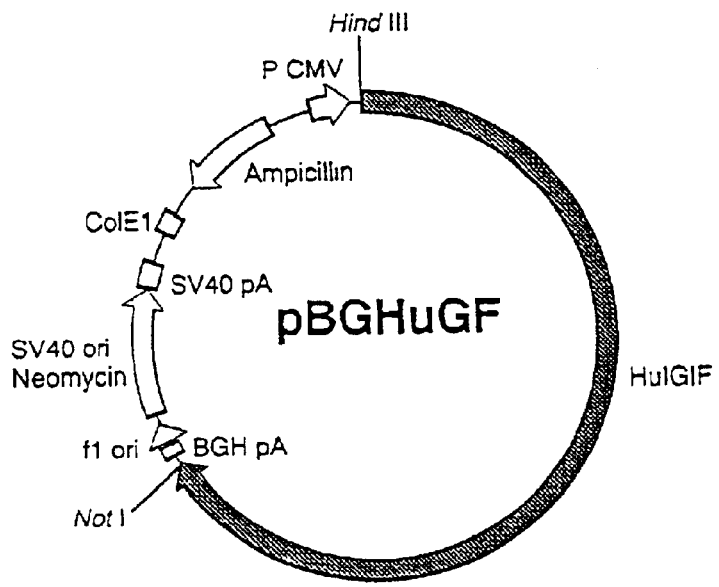
FIG. 4 shows the structure of the recombinant DNA pBGHuGF.

According to the method in Japanese Patent Application No. 185,305/96 by the same applicant of the present invention, an autonomously-replicable recombinant DNA, pBGHuGF, linked to a chromosomal DNA encoding human IL-18, was obtained. Dideoxyribonucleotide sequencing analysis revealed that as shown in FIG. 4, in the recombinant DNA, a chromosomal DNA, which encodes human IL-18, i.e., DNA HuIGIF with SEQ ID NO: 17, was linked to the downstream of a restriction site by a restriction enzyme, Hind III. As shown in SEQ ID NO: 17, the chromosomal DNA HuIGIF consists of 11,464 bp where the exon was fragmented by four introns positioning at nucleotides 83–1, 453, 1,466–4,848, 4,984–6,317, and 6,452–11,224. Among the resting nucleotide sequence excluding these introns, nucleotides 3–11,443 from the 5'-terminus are the part that encodes a precursor of human IL-18, and nucleotides 4,866–4,983 are the part that encodes an active human IL-18. The chromosomal DNA contained nucleotides sequences encoding SEQ ID NOs: 1 to 5; these amino acid sequences were respectively encoded by nucleotides 4,911–4,928, 4,953–4,970, 11,372–11,392, 6,350–6,364, and 6,413–6,427 in SEQ ID NO: 17.

According to the method in Japanese Patent Application No. 185,305/96, the recombinant DNA pBGHuGF was introduced into CHO-K1 cells, ATCC CCL 61, an established cell line derived from Chinese hamster ovary, followed by culturing the cells. The culture supernatant was contacted with a supernatant of cell disruptant prepared from a THP-1 cell culture to produce a polypeptide which was then purified by immunoaffinity chromatography to obtain a purified human IL-18 in a yield of about 15 mg/l culture. According to the method in Japanese Patent Application No. 185,305/96, the polypeptide was analyzed and determined for biological activity and physicochemical property as indicated below: It was confirmed that human lymphocytes, which were collected from a healthy donor, produced IFN-γ depending on the purified human IL-18 concentration when cultured at different concentrations of the human IL-18, revealing that the human IL-18 has a biological activity of inducing IFN-γ production by lymphocytes as an immunocompetent cell. In accordance with the method as reported by U. K. Laemmli in *Nature*, Vol. 227, pp. 680–685 (1970), the purified human IL-18 was subjected to SDS-PAGE in the presence of 2 w/v % dithiothreitol as a reductant, resulting in a major band with an IFN-γ inducing activity at a position corresponding to 18,000–19,500 daltons. The N-terminal region of the human IL-18 contained the amino acid sequence of SEQ ID NO: 15 which completely corresponded to the amino acid sequence in the N-terminal region of SEQ ID NO: 17 for an active IL-18.

Experiment 6
Preparation of Mouse IL-18

To a 0.5-ml reaction tube were added 8 μl of 25 mM magnesium chloride, 10 μl of 10×PCR buffer, one μl of 25 mM dNTP mix, one μl of 2.5 units/μl of amplitaq DNA polymerase, one ng of a recombinant DNA, which encodes mouse IL-18 having the nucleotide sequence of SEQ ID NO: 18 and the amino acid sequence of SEQ ID NO: 7, prepared from a phage DNA clone according to the method in Japanese Patent Kokai No. 27,189/96, and adequate amounts of a sense and antisense primers having nucleotide sequences represented by 5'-ATAGAATTCAAATGAACTTTGGCCGACTTCACTG-3' and 5'-ATAAAGCTTCTAACTTTGATGTAAGTT-3', respectively, which were chemically synthesized based on the amino acid sequences nearness to the N- and C-termini of SEQ ID NO: 7, and the mixture solution was brought up to a volume of 100 μl with sterilized distilled water. The solution thus obtained was subjected in a usual manner to PCR reaction of the following three cycles of successive incubations at 94° C. for one minute, 43° C. for one minute, and 72° C. for one minute, and further 40 cycles of successive incubations at 94° C. for one minute, 60° C. for one minute, and 72° C. for one minute.

The product obtained by the PCR reaction and "pCR-Script SK (+)", a plasmid vector commercialized by Stratagene Cloning Systems, California, USA, were in a conventional manner ligated together using a DNA ligase into a recombinant DNA which was then introduced into "XL-1 Blue MRF'Kan", an *Escherichia coli* strain commercialized by Stratagene Cloning Systems, California, USA., to obtain a transformant. The transformant was inoculated to L-broth (pH 7.2) containing 50 μg/ml ampicillin, followed by the incubation at 37° C. for 18 hours under shaking conditions. The culture was centrifuged to obtain the proliferated transformants which were then treated with a conventional alkali-SDS method to isolate a recombinant DNA. A portion of the recombinant DNA isolated was analyzed by dideoxyribonucleotide sequencing, revealing that the recombinant DNA contained restriction sites of Eco RI and Hind III at the 5'- and 3'-termini of SEQ ID NO: 18, respectively, and a DNA containing a methionine codon for initiating polypeptide synthesis and a TAG codon for terminating polypeptide synthesis, which were located in just before and after the N- and C-termini of the amino acid sequence as shown in parallel in SEQ ID NO: 18. The recombinant DNA contained the nucleotide sequences of SEQ ID NOs: 1 to 5. These amino acid sequences were encoded by nucleotides 46–63, 85–102, 394–414, 148–162, and 211–225 in SEQ ID NO: 18.

Figure 5:
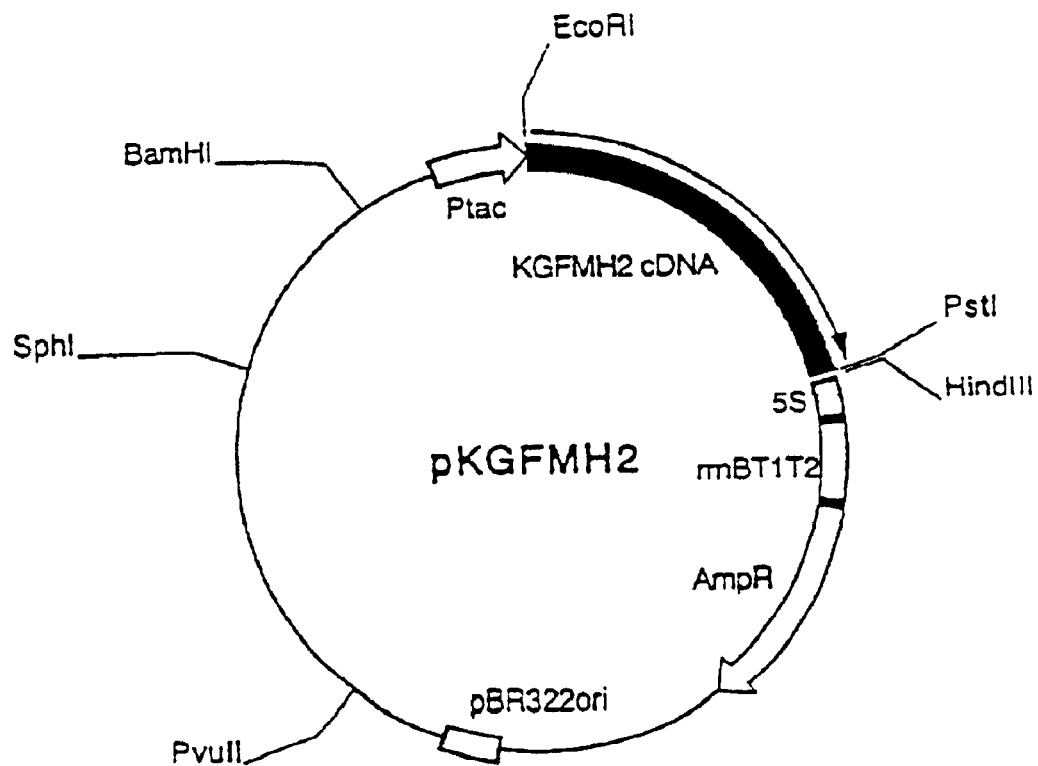
FIG. 5 shows the structure of the recombinant DNA pKGFMH2.

The remaining portion of the recombinant DNA was in a conventional manner cleaved with restriction enzymes of Eco RI and Hind II, and the resulting 0.1 μg of an Eco RI-Hind III DNA fragments, obtained by using "DNA LIGATION KIT VER 2", a DNA ligation kit commercialized by Takara Shuzo Co., Ltd., Tokyo, Japan, and 10 ng of pKK223-3, a plasmid vector commercialized by Pharmacia LKB Biotechnology AB, Uppsala, Sweden, which had been cleaved with a restriction enzyme were linked together, by incubating at 16° C. for 30 min to obtain an autonomously-replicable recombinant DNA, pKGFMH2. Using competent cell method, an *Escherichia coli* Y1090 strain, ATCC 37197, was transformed using the recombinant DNA pKGFMH2, and the resulting transformant, KGFMH2, was inoculated to L-broth (pH 7.2) containing 50 μg/ml ampicillin, and cultured at 37° C. for 18 hours under shaking conditions. The culture was centrifuged to collect the proliferated transformants, followed by applying a conventional SDS-alkali method to a portion of the transformants to extract the recombinant DNA pKGFMH2. Dideoxyribonucleotide sequencing analysis revealed that, as shown in FIG. 5, KGFMH2 cDNA containing the nucleotide sequence of SEQ ID NO: 18 was linked to the downstream of the Tac promoter in the recombinant DNA pKGFMH2.

Ampicillin was added to L-broth (pH 7.2), which had been sterilized by autoclaving, to give a concentration of 50 μg/ml, cooled to 37° C., and inoculated with the transformant KGFMH2, followed by the culture at 37° C. for 18 hours. Eighteen liters of a fresh preparation of the same culture medium was placed in a 20-l jar fermenter, similarly sterilized as above, admixed with ampicillin, cooled to 37° C., and inoculated with one v/v % of the seed culture obtained in the above, followed by the culture at 37° C. for 8 hours under aeration-agitation conditions. The resulting culture was centrifuged to collect the cultured cells which were then suspended in a mixture solution (pH 7.3) containing 150 mM sodium chloride, 16 mM disodium hydrogenphosphate, and 4 mM sodium dihydrogenphosphate, disrupted by ultrasonication, and centrifuged to remove cell disruptant, and this yielded an about two liters of a supernatant.

To an about two liters of the supernatant was added 10 mM phosphate buffer (pH 7.3) containing ammonium sulfate to give a 40% ammonium saturation. The resulting sediment was removed by centrifugation, and the supernatant was mixed with ammonium sulfate to give an 85% ammonium saturation, allowed to stand at 4° C. for 18 hours, and centrifuged at about 8,000 rpm for 30 min to obtain a newly formed sediment. The sediment thus obtained was dissolved in 10 mM phosphate buffer (pH 6.6) containing 1.5 M ammonium sulfate to give a total volume of about 1,300 ml, and the solution was filtered, and fed to a column packed with about 800 ml of "PHENYL SEPHAROSE CL-6B", a gel commercialized by Pharmacia LKB Biotechnology AB, Uppsala, Sweden, followed by washing the column with a fresh preparation of the same buffer and feeding to the column a linear gradient buffer of ammonium sulfate decreasing from 1.5 M to 0 M in 10 mM phosphate buffer (pH 6.6) at an SV (space velocity) 1.5. Fractions eluted at around 1 M ammonium sulfate were pooled, concentrated using a membrane filter, and dialyzed against 10 mM phosphate buffer (pH 6.5) at 4° C. for 18 hours. The dialyzed solution was fed to a column packed with about 55 ml of "DEAE-5PW", a gel commercialized by Pharmacia LKB Biotechnology AB, Uppsala, Sweden, which had been equilibrated with 10 mM phosphate buffer (pH 6.5). The column was washed with a fresh preparation of the same buffer, and fed with a linear gradient buffer of sodium chloride increasing from 0 M to 0.5 M in 10 mM phosphate buffer (pH 6.5) at SV 5.5, followed by collecting fractions eluted at around 0.2 M sodium chloride. Thereafter, the fractions were pooled and concentrated similarly as above up to give an about nine milliliters, followed by dialyzing the concentrate against PBS (phosphate buffered saline) at 4° C. for 18 hours, and feeding the dialyzed solution to a column packed with "SUPERDEX 75", a gel commercialized by Pharmacia LKB Biotechnology AB, Uppsala, Sweden, which had been equilibrated with a fresh preparation of the same PBS. The column was fed with a fresh preparation of the same PBS to collect fractions with an IFN-γ inducing activity, and the fractions were pooled and concentrated with a membrane filter to obtain a purified mouse IL-18 in a yield of about 350 μg/l culture.

According to the method in Japanese Patent Kokai No. 27,189/96, the purified mouse IL-18 was analyzed and determined for biological activity and physicochemical property as indicated below: Culturing mouse spleen cells, collected by a conventional manner, under different concentrations of the mouse IL-18 resulted in an IFN-γ production depending on the concentrations of the mouse IL-18, and this revealed that the mouse IL-18 has an activity of inducing IFN-γ production by spleen cells as an immunocompetent cell. In accordance with the method as reported by U. K. Laemmli in *Nature*, Vol. 227, pp. 680–685 (1970), the purified human IL-18 was subjected to SDS-PAGE under non-reducing conditions, resulting in a major band with an IFN-γ inducing activity at a position corresponding to 19,000±5,000 daltons. The N-terminal region of the mouse IL-18 contained the amino acid sequence of SEQ ID NO: 19 which corresponded to the N-terminal region of SEQ ID NO: 18.

With reference to Experiment 7, the biological activity of the IL-18 according to the present invention will be described in more detail, and Experiment 8 describes the cytotoxicity of the IL-18:

Experiment 7
Biological Activity
Experiment 7-1
Induction of GM-CSF Production

Using a heparinized syringe, blood was collected from a healthy volunteer and diluted two fold with serum-free RPMI 1640 medium (pH 7.4). The diluent was overlaid on a ficoll and centrifuged, and the collected lymphocytes were washed with RPMI 1640 medium (pH 7.4) supplemented with 10 v/v % fetal calf serum, and suspended in a fresh preparation of the same medium to give a cell density of $1 \times 10^6$ cells/ml, followed by distributing the cell suspension to a 12-well microplate by two ml/well.

Using RPMI 1640 medium (pH 7.4) supplemented with 10 v/v % fetal calf serum, an IL-18 preparation obtained by the method in Experiment 1 was prepared into a one μg/ml solution which was then distributed to the above microplate by 20–200 μl/well. To the microplate was further added a fresh preparation of the same buffer, supplemented with 500 μl/ml of Concanavalin A, by 10 μl/well, followed by the incubation at 37° C. for 48 hours in a 5 v/v % $CO_2$ incubator. After completion of the culture, supernatants in each well were sampled by 0.1 ml/well, and determined for GM-CSF content using a conventional enzyme immunoassay. In parallel, a culture system free of IL-18 as a control was provided and treated similarly as above. The data is in Table 1:

TABLE 1

| IL-18* (nM) | GM-CSF yield (pg/ml) |
|---|---|
| 0 | 510 |
| 0.7 | 2,150 |
| 2.8 | 3,050 |
| 5.6 | 3,950 |

Note:
The symbol "*" means that IL-18 was added to the culture system in the presence of 2.5 μg/ml of Concanavalin A.

The results in Table 1 indicate that lymphocytes as an immunocompetent cell produced GM-CSF depending on the concentration of IL-18 when contacted with IL-18 in the presence of Concanavalin A as a cofactor. It was also confirmed that all of the IL-18 preparations and functional equivalents thereof, which were obtained by the methods in Experiments 2 to 5, induced GM-CSF production even when used alone similarly as above. An IL-18 preparation obtained by the method in Experiment 6 was tested in accordance with Experiment 7-1 except that the human lymphocytes used in the experiment were replaced with spleen cells prepared from mouse by a conventional manner, revealing that the IL-18 preparation also induced GM-CSF production.

Experiment 7-2
Inhibition of Osteoclast Formation
Experiment 7-2(a)

As reported by T. J. Martin and K. W. Ng in *Journal of Cellular Biochemistry*, Vol. 56, pp. 357–366 (1994), it is considered requisite for contacting osteoclastic precursor cells, derived from hematopoietic stem cells, with osteoblasts or bone marrow stromas to generally differentiate osteoclastic precursor cells into mature osteoclasts. As described by G. D. Roodman in *Endocrine Reviews*, Vol. 17, No. 4, pp. 308–332 (1996), it is generally recognized that osteoclasts have characters of multinucleated cells, tartaric acid-resistant acid phosphatase (hereinafter abbreviated as "TRAP") activity, and a calcitonin receptor. In a co-culture system of osteoblasts and bone marrow cells as reported by Nobuyuki UDAGAWA et al., in *Journal of Experimental Medicine*, Vol. 182, pp. 1,461–1,468 (1995), these cells respond to factors such as $1\alpha,25$-dihydroxyvitamin $D_3$, prostaglandin $E_2$, adrenocortical hormone, interleukin 1, interleukin 6, and interleukin 11, to form osteoclast-like cells (hereinafter may be abbreviated as "OCL"). The formed OCL has characters of osteoclasts in vivo. Therefore, the co-culture system well reflects in vitro the processes of osteoclast formation in vivo. Using this system, experiments for osteoclast formation and osteoclastgenic inhibitory agents can be carried out.

The osteoclastgenic inhibitory activity of the IL-18 according to the present invention was studied using the above co-culture system. The osteoblasts used in this experiment were prepared in a conventional manner by treating a newborn mouse calvaria with 0.1 w/v % collagenase commercialized by Worthington Biochemical Co., Freefold, Australia, and 0.2 w/v % dispase commercialized by Godo Shusei Co., Ltd., Tokyo, Japan. The bone marrow cells were prepared from a mature mouse in a conventional manner. As a negative control, $2\times10^4$ cells of a primary cell culture of osteoblasts and $5\times10^5$ cells of bone marrow cells were co-cultured in each well of a 48-well microplate containing 0.4 ml/well of α-MEM medium supplemented with 10 v/v % fetal calf serum (hereinafter designated as "Medium" throughout Experiment 4-2) at 37° C. for seven days in a 5 v/v % $CO_2$ incubator. As a positive control, the above two-types of cells were co-cultured similarly as in the negative control except that they were cultured in other wells containing $10^{-8}$M of 1α,25-dihydroxyvitamin $D_3$ commercialized by Wako Pure Chemicals, Tokyo, Japan, and $10^{-7}$M of prostaglandin $E_2$ commercialized by Sigma Chemical Company, Missouri, USA. The aforesaid two-types of cells were co-cultured similarly as in the positive control except that they were cultured in other wells containing 1α,25-dihydroxyvitamin $D_3$ commercialized by Wako Pure Chemicals, Tokyo, Japan, and prostaglandin $E_2$ commercialized by Sigma Chemical Company, Missouri, USA., in the same concentrations as used in the positive control, and a concentration of 0.01–10 ng/ml of an IL-18 preparation prepared by the method in Experiment 6. In every co-culture system, the media in each well were replaced with fresh preparations of the same media used in the co-culture systems on the 3rd day after the initiation of each culture. According to the method by Nobuyuki UDAGAWA in *Journal of Experimental Medicine*, Vol. 182, pp. 1,461–1,468 (1995), the cells on the 6th day after the initiation of each culture were fixed and stained based on TRAP activity, followed by counting the stained cells (hereinafter called "TRAP-positive cells") per well. Throughout Experiment 4-2, quadruplet wells under the same conditions were provided for each co-culture system, and the mean value for the TRAP-positive cells per well in each system was calculated. The results are in Table 2:

TABLE 2

| IL-18 (ng/ml) | Osteoclastgenic formation factor*1 | Number of TRAP-positive cells per well*2 |
|---|---|---|
| 0 | − | 2 |
| 0 | + | 110 |
| 0.01 | + | 114 |
| 0.1 | + | 111 |
| 0.5 | + | 106 |
| 1 | + | 63 |
| 2 | + | 29 |
| 4 | + | 12 |
| 8 | + | 2 |
| 10 | + | 2 |

Note:
*1: The symbols of "+" and "−" show co-culture systems with and without $10^{-8}$M 1α, 25-dihydroxyvitamin $D_3$ and $10^{-7}$M prostaglandin $E_2$, respectively.
*2: It shows a mean value of the data from quadruplet wells cultured under the same conditions.

As shown in Table 2, the formation of TRAP-positive cells was not substantially observed in the negative control, but the distinct formation was observed in the positive control. In the co-culture systems, i.e., the positive control supplemented additionally with IL-18, the formation of TRAP-positive cells was inhibited depending on the concentration of IL-18, and the maximum inhibition, i.e., a level equal to that in the negative control, was found at eight ng/ml or more of IL-18. These data strongly indicates that IL-18 has a concrete activity of inhibiting OCL formation in vitro and also inhibits osteoclast formation.

Experiment 7-2(b)

As described hereinbefore, it was confirmed that there exist factors that induce the formation of osteoclast-like cells in the co-culture systems used throughout Experiment 7-2. Therefore, in this Experiment 7-2(b), it was studied whether the inhibitory activity of IL-18 on osteoclast formation observed in Experiment 7-2(a) was specific to some factors or not; the osteoclast-like cells were cultured by the same method as used in the negative control in Experiment 7-2(a) except for using a medium supplemented with $10^{-8}$M 1α,25-dihydroxyvitamin $D_3$, $10^{-7}$M prostaglandin $E_2$, 200 ng/ml parathyroid hormone, 100 ng/ml interleukin 1, or 20 ng/ml interleukin 11. These culture systems were for positive controls. In parallel, the cells were cultured in other wells by the same method used in the positive controls except for using a medium containing 10 ng/ml of an IL-18 preparation obtained by the method in Experiment 6, in addition to any one of the above factors at the same concentration. After completion of the cultures, TRAP-positive cells in each well were counted, and the numbers were compared similarly as the Experiment 7-2(a). The results are in Table 3:

TABLE 3

| Osteoclast formation factor*1 (concentration) | | IL-18*2 | Number of TRAP-positive cells per well*3 |
|---|---|---|---|
| $D_3$ | ($10^{-8}$M) | − | 94 |
| | | + | 3 |
| $PGE_2$ | ($10^{-7}$M) | − | 77 |
| | | + | 3 |
| PTH | (200 ng/ml) | − | 63 |
| | | + | 3 |
| IL-11 | (100 ng/ml) | − | 84 |
| | | + | 3 |
| IL-1 | (20 ng/ml) | − | 71 |
| | | + | 3 |

Note:
*1: $D_3$, $PGE_2$, PTH, IL-11, and IL-1 are respectively 1α, 25-dihydroxyvitamin $D_3$, prostaglandin $E_2$, parathyroid hormone, interleukin-11, and interleukin-1 which were added to wells to give the concentrations as indicated in parentheses.
*2: The symbol "+" means that IL-18 was added to a well to give a concentration of 10 ng/ml, and the symbol "−" means that IL-18 was not added to.
*3: It shows a mean value of the data from quadruplet wells cultured under the same conditions.

As shown in Table 3, a distinct formation of TRAP-positive cells was observed in every positive control, but the formation was almost completely inhibited in the presence of IL-18. This strongly indicates that IL-18 has a wide and general activity of inhibiting osteoclast formation independently of osteoclast-formation-related factors.

Experiment 7-2(c)

It was studied whether the osteoclastgenic inhibition by IL-18, confirmed in Experiments 7-2(a) and 7-2(b), was caused by the action of the IL-18-induced GM-CSF. For positive and negative controls, the same co-culture systems employed in Experiment 7-2(a) were used. Using other wells, the co-culture of osteoblasts and bone marrow cells was carried out similarly as the method used for the positive controls except for using a medium supplemented with 1α,25-dihydroxyvitamin $D_3$ and prostaglandin $E_2$ at the same concentrations used in the positive control, and with (i)

10 μg/ml of an anti-mouse GM-CSF polyclonal antibody commercialized by R&D Systems, Minnesota, USA, (ii) 10 ng/ml of an IL-18 preparation obtained by the method in Experiment 6, (iii) (ii) plus 10 μg/ml of an anti-mouse polyclonal antibody, (iv) 0.1 ng/ml of a mouse GM-CSF commercialized by R&D Systems, Minnesota, USA, or (v) (iv) plus 10 μg/ml of an anti-mouse GM-CSF polyclonal antibody. After completion of the culture, TRAP-positive cells in each well were counted, and the numbers were compared similarly as in Experiment 7-2(a). The data is shown in Table 4 where the symbols "i" to "v" coincide with those used in the co-culture systems other than the control systems.

IL-18 has substantially no serious side effects. These facts indicate that the osteoclastgenic inhibitory agent according to the present invention can be successively administered to warm-blooded animals in general and including humans to induce osteoclast formation and exert a satisfactory therapeutic and/or prophylactic effect on osteoclast-related diseases without causing serious side effects.

The following Examples describe the present osteoclastgenic inhibitory agent according to the present invention:

EXAMPLE 1

Liquid

Either of IL-18 preparations, obtained by the methods in Experiments 1 to 6, was dissolved in physiological saline

TABLE 4

| Culture system*1 | Osteoclastgenic factor*2 | IL-18*3 | GM-CSF*4 | Anti-GM-CSF antibody*5 | Number of TRAP-positive cells per well*6 |
|---|---|---|---|---|---|
| N | − | − | − | − | 3 |
| P | + | − | − | − | 122 |
| i | + | − | − | + | 112 |
| ii | + | + | − | − | 3 |
| iii | + | + | − | + | 111 |
| iv | + | − | + | − | 4 |
| v | + | − | + | + | 106 |

Note:
*1; where the symbols "N" and "P" mean negative and positive controls, respectively, and the symbols "i" to "v" correspond to those in the five types co-culture systems used.
*2; where the symbol "+" means that 1α,25-dihydroxyvitamin $D_3$ and prostaglandin $E_2$ were respectively added to a well to give respective concentrations of $10^{-8}$M and $10^{-7}$M, and the symbol "−" means that these compounds were not added to.
*3; The symbol "+" means that IL-18 was added to a well to give a concentration of 10 ng/ml, and the symbol "−" means that IL-18 was not added to.
*4; The symbol "+" means that GM-CSF was added to a well to give a concentration of 0.1 ng/ml, and the symbol "−" means that GM-CSF was not added to.
*5; The symbol "+" means that an anti-GM-CSF polyclonal antibody was added to a well to give a concentration of 10 μg/ml, and the symbol "−" means that the polyclonal antibody was not added to.

As shown in Table 4, the formation of TRAP-positive cells was almost completely inhibited by IL-18, cf., the co-culture system (ii), but the inhibition was almost completely inhibited by the addition of the anti-mouse polyclonal antibody, cf., the co-culture system (iii). Mouse GM-CSF exhibited an activity of inhibiting the formation of TRAP-positive cells similar to IL-18, cf., the co-culture system (iv), and the inhibition was almost completely inhibited by the addition of the anti-mouse GM-CSF polyclonal antibody, cf., the co-culture system (v). The sole use of the anti-mouse GM-CSF polyclonal antibody gave no influence on the formation of TRAP-positive cells, cf., the co-culture system (i). These data strongly indicates that the osteoclastgenic inhibition by IL-18 was due to the action of the IL-18-induced GM-CSF.

Experiment 8

Acute Toxicity Test

Eight-week-old mice were in a conventional manner injected percutaneously, orally, or intraperitoneally with either of IL-18 preparations obtained by the methods in Experiments 1 to 6. The results showed that these IL-18 preparations had an $LD_{50}$ of about one mg/kg or more in mice independent of the route of administration. The data evidences that IL-18 can be incorporated into pharmaceuticals for warm-blooded animals in general and including humans without causing no serious side effects.

As described in *Nikkei Biotechnology Annual Report 1996*, pp. 498–499 (1995), published by Nikkei BP Publisher, Tokyo, Japan (1995), the IL-18-induced GM-CSF has not yet been clinically used in Japan, but applied clinically in USA and Europe. The fact would show that containing one w/v % human serum albumin as a stabilizer to give a concentration of two mg/ml of the IL-18 preparation. The resulting solutions were in a conventional manner membrane filtered for sterilization into liquids.

The liquids have a satisfactory stability and can be arbitrarily used as ingredients for cell culture and agents in the form of an injection, ophthalmic solution, or collunarium for regulating bone resorption and for osteoclast-related diseases, directed to treat and/or prevent hypercalcemia, osteoclastoma, osteoporosis, etc.

EXAMPLE 2

Dry Agent

Fifty milligrams of either of IL-18 preparations, obtained by the methods in Experiments 1 to 6, was dissolved in 100 ml of physiological saline containing one w/v % purified gelatin as a stabilizer. The solutions thus obtained were in a conventional manner membrane filtered for sterilization, distributed to vials by one milliliter, lyophilized, and sealed with caps.

The products have a satisfactory stability and can be arbitrarily used as ingredients for cell culture and agents in the form of a dry injection for regulating bone resorption and for osteoclast-related diseases, directed to treat and/or prevent hypercalcemia, osteoclastoma, osteoporosis, etc.

EXAMPLE 3

Dry Agent

Fifty milligrams of either of IL-18 preparations, obtained by the methods in Experiments 1 to 6, was dissolved in 100 ml of physiological saline containing one w/v % trehalose as a stabilizer. The solutions were in a conventional manner membrane filtered for sterilization, distributed to vials by one milliliter, lyophilized, and sealed with caps.

The products have a satisfactory stability and can be arbitrarily used as ingredients for cell culture and agents in the form of a dry injection for regulating bone resorption and for osteoclast-related diseases, directed to treat and/or prevent hypercalcemia, osteoclastoma, osteoporosis, etc.

EXAMPLE 4

Ointment

"HIVIS WAKO GEL® 104", a carboxyvinylpolymer commercialized by Wako Pure Chemical Industries, Ltd., Tokyo, Japan, and a high-purity trehalose were dissolved in a sterilized distilled water to give respective concentrations of 1.4 w/w % and 2.0 w/w %, and the solution was mixed to homogeneity with either of IL-18 preparations obtained by the methods in Experiments 1 to 6, and adjusted to pH 7.2 to obtain a paste containing about one mg of an IL-18 preparation per g of the product.

Each product thus obtained has a satisfactory spreadability and stability and can be arbitrarily used as an agent in the form of an ointment for regulating bone resorption and for osteoclast-related diseases, directed to treat and/or prevent hypercalcemia, osteoclastoma, osteoporosis, etc.

EXAMPLE 5

Tablet

"FINETOSE®", an anhydrous crystalline α-maltose powder commercialized by Hayashibara Biochemical Laboratories, Inc., Okayama, Japan, was mixed to homogeneity with either of IL-18 preparations, obtained by the methods in Experiments 1 to 6, and "LUMIN" or 1-1'-1"-trihepthyl-11-chinolyl(4).4.4'-penthamethinchynocyan-1,1"-dijodide. The mixtures were in a conventional manner tabletted to obtain tablets, about 200 mg weight each, containing an about two milligrams of either of the IL-18 preparations and an about two milligrams of LUMIN per tablet.

The products have a satisfactory swallowability, stability, and cell-activating activity and can be arbitrarily used as agents in the form of a tablet for regulating bone resorption and for osteoclast-related diseases, directed to treat and/or prevent hypercalcemia, osteoclastoma, osteoporosis, etc.

As described above, the osteoclastgenic inhibitory agent according to the present invention effectively inhibits osteoclast formation. Therefore, the agent can be arbitrarily used as an ingredient for cell culture and agents for regulating bone resorption and for osteoclast-related diseases, directed to treat and/or prevent hypercalcemia, osteoclastoma, osteoporosis, etc.

Thus the present invention with these useful activities and functions is a significant invention that would greatly contribute to this field.

While there has been described what is at present considered to be the preferred embodiments of the invention, it will be understood the various modifications may be made therein, and it is intended to cover in the appended claims all such modifications as fall within the true spirits and scope of the invention.

What is claimed is:

1. A method for treating a disease associated with excessive osteoclast formation or activity, comprising administering to a patient suffering from said disease an effective amount of either interleukin-18 or its functional equivalent, said functional equivalent consisting of an amino acid sequence where one or more cysteine residues in the amino acid sequence of interleukin-18 are replaced with other amino acid residues and/or where one or more amino acid residues are added to the N- and/or C-terminus of interleukin-18 in such a manner that said replacement with other amino acid residues and/or said addition of amino acid residues to the N- and/or C-terminus does not completely eliminate the osteoclastgenic inhibitory activity of said interleukin-18.

2. The method of claim 1 which is to treat arthropathy, deformity ostitis, osteopenia, osteoclastoma, osteosarcoma, or osteoporosis.

3. The method of claim 1, wherein said interleukin-18 is of human origin.

4. The method of claim 1, wherein said osteoclastgenic inhibitory composition further comprises a stabilizer selected from the group consisting of proteins, buffers, saccharides, and mixtures thereof.

5. The method of claim 1, wherein said osteoclastgenic inhibitory composition is in the form of a liquid, a paste, or a solid.

* * * * *

```
                           SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal fragment (xi) SEQUENCE DESCRIPTION: SEQ ID NO: 1:

Asn Asp Gln Val Leu Phe
1               5

(2) INFORMATION FOR SEQ ID NO: 2:

(i) SEQUENCE CHARACTERISTICS:
        (A) LENGTH: 6 amino acids
        (B) TYPE: amino acid
        (D) TOPOLOGY: linear (ii) MOLECULE TYPE: internal fragment (xi) SEQUENCE DESCRIPTION: SEQ ID NO: 2:

Phe Glu Asp Met Thr Asp
1               5

(2) INFORMATION FOR SEQ ID NO: 3:
```

```
        (i) SEQUENCE CHARACTERISTICS:
            (A) LENGTH: 7 amino acids
            (B) TYPE: amino acid
            (D) TOPOLOGY: linear (ii) MOLECULE TYPE: peptide (v) FRAGMENT TYPE: internal fragment (xi) SEQUENCE DESCRIPTION: SEQ ID NO: 3:

Phe Lys Leu Ile Leu Lys Lys
1               5

(2) INFORMATION FOR SEQ ID NO: 4:

(i) SEQUENCE CHARACTERISTICS:
            (A) LENGTH: 5 amino acids
            (B) TYPE: amino acid
            (D) TOPOLOGY: linear (ii) MOLECULE TYPE: internal fragment (xi) SEQUENCE DESCRIPTION: SEQ ID NO: 4:

Met Tyr Lys Asp Ser
1               5

(2) INFORMATION FOR SEQ ID NO: 5:

(i) SEQUENCE CHARACTERISTICS:
            (A) LENGTH: 5 amino acids
            (B) TYPE: amino acid
            (D) TOPOLOGY: linear (ii) MOLECULE TYPE: internal fragment (xi) SEQUENCE DESCRIPTION: SEQ ID NO: 5:

Ser Thr Leu Ser Cys
1               5

(2) INFORMATION FOR SEQ ID NO: 6:

(i) SEQUENCE CHARACTERISTICS:
            (A) LENGTH: 157 amino acids
            (B) TYPE: amino acid
            (D) TOPOLOGY: linear (ii) MOLECULE TYPE: peptide (xi) SEQUENCE DESCRIPTION: SEQ ID NO: 6:

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
                20                  25                  30

Met Thr Asp Ser Asp Cys Arg Asp Asn Ala Pro Arg Thr Ile Phe Ile
            35                  40                  45

Ile Ser Met Tyr Lys Asp Ser Gln Pro Arg Gly Met Ala Val Thr Ile
        50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
```

```
                115                 120                 125
Lys Glu Arg Asp Leu Phe Lys Leu Ile Leu Lys Lys Glu Asp Glu Leu
            130                 135                 140

Gly Asp Arg Ser Ile Met Phe Thr Val Gln Asn Glu Asp
145                 150                 155

(2) INFORMATION FOR SEQ ID NO: 7:

(i) SEQUENCE CHARACTERISTICS:
        (A) LENGTH: 157 amino acids
        (B) TYPE: amino acid
        (D) TOPOLOGY: linear (ii) MOLECULE TYPE: peptide (xi) SEQUENCE DESCRIPTION: SEQ ID NO: 7:

Asn Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
                20                  25                  30

Thr Asp Ile Asp Gln Ser Ala Ser Glu Pro Gln Thr Arg Leu Ile Ile
            35                  40                  45

Tyr Met Tyr Lys Asp Ser Glu Val Arg Gly Leu Ala Val Thr Leu Ser
50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Arg Val Pro Gly His Asn Lys Met Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Asp Glu Asn Gly Asp
        130                 135                 140

Lys Ser Val Met Phe Thr Leu Thr Asn Leu His Gln Ser
145                 150                 155

(2) INFORMATION FOR SEQ ID NO: 8:

(i) SEQUENCE CHARACTERISTICS:
        (A) LENGTH: 471 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: liver (ix) FEATURE:
        (A) NAME/KEY: mat peptide
        (B) LOCATION: 1..471
        (C) IDENTIFICATION METHOD: E (xi) SEQUENCE DESCRIPTION: SEQ ID NO: 8:

TAC TTT GGC AAG CTT GAA TCT AAA TTA TCA GTC ATA AGA AAT TTG AAT      48
Tyr Phe Gly Lys Leu Glu Ser Lys Leu Ser Val Ile Arg Asn Leu Asn
1               5                   10                  15

GAC CAA GTT CTC TTC ATT GAC CAA GGA AAT CGG CCT CTA TTT GAA GAT      96
Asp Gln Val Leu Phe Ile Asp Gln Gly Asn Arg Pro Leu Phe Glu Asp
                20                  25                  30
```

```
ATG ACT GAT TCT GAC TGT AGA GAT AAT GCA CCC CGG ACC ATA TTT ATT      144
Met Thr Asp Ser Asp Cys Arg Asp Asn Ala Pro Arg Thr Ile Phe Ile
        35                  40                  45

ATA AGT ATG TAT AAA GAT AGC CAG CCT AGA GGT ATG GCT GTA ACT ATC      192
Ile Ser Met Tyr Lys Asp Ser Gln Pro Arg Gly Met Ala Val Thr Ile
    50                  55                  60

TCT GTG AAG TGT GAG AAA ATT TCA ACT CTC TCC TGT GAG AAC AAA ATT      240
Ser Val Lys Cys Glu Lys Ile Ser Thr Leu Ser Cys Glu Asn Lys Ile
65                  70                  75                  80

ATT TCC TTT AAG GAA ATG AAT CCT CCT GAT AAC ATC AAG GAT ACA AAA      288
Ile Ser Phe Lys Glu Met Asn Pro Pro Asp Asn Ile Lys Asp Thr Lys
            85                  90                  95

AGT GAC ATC ATA TTC TTT CAG AGA AGT GTC CCA GGA CAT GAT AAT AAG      336
Ser Asp Ile Ile Phe Phe Gln Arg Ser Val Pro Gly His Asp Asn Lys
                100                 105                 110

ATG CAA TTT GAA TCT TCA TCA TAC GAA GGA TAC TTT CTA GCT TGT GAA      384
Met Gln Phe Glu Ser Ser Ser Tyr Glu Gly Tyr Phe Leu Ala Cys Glu
            115                 120                 125

AAA GAG AGA GAC CTT TTT AAA CTC ATT TTG AAA AAA GAG GAT GAA TTG      432
Lys Glu Arg Asp Leu Phe Lys Leu Ile Leu Lys Lys Glu Asp Glu Leu
    130                 135                 140

GGG GAT AGA TCT ATA ATG TTC ACT GTT CAA AAC GAA GAC                  471
Gly Asp Arg Ser Ile Met Phe Thr Val Gln Asn Glu Asp
145                 150                 155

(2) INFORMATION FOR SEQ ID NO: 9:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: N-terminal fragment (xi) SEQUENCE DESCRIPTION: SEQ ID NO: 9:

Met Tyr Phe Gly Lys Leu Glu Ser Lys Leu Ser
1               5                   10

(2) INFORMATION FOR SEQ ID NO: 10:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: C-terminal fragment (xi) SEQUENCE DESCRIPTION: SEQ ID NO: 10:

Ser Ile Met Phe Thr Val Gln Asn Glu Asp
1               5                   10

(2) INFORMATION FOR SEQ ID NO: 11:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (v) FRAGMENT TYPE: N-terminal fragment
```

(xi) SEQUENCE DESCRIPTION: SEQ ID NO: 11:

Tyr Phe Gly Lys Leu Glu Ser Lys Leu Ser Val Ile Arg
1               5                   10

(2) INFORMATION FOR SEQ ID NO: 12:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal fragment (xi) SEQUENCE DESCRIPTION: SEQ ID NO: 12:

Thr Ile Phe Ile Ile Ser Met Tyr Lys Asp Ser Gln Pro Arg
1               5                   10

(2) INFORMATION FOR SEQ ID NO: 13:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (v) FRAGMENT TYPE: internal fragment (xi) SEQUENCE DESCRIPTION: SEQ ID NO: 13:

Ile Ile Ser Phe Lys Glu Met Asn Pro Pro Asp Asn Ile Lys Asp Thr Lys
1               5                   10                  15

(2) INFORMATION FOR SEQ ID NO: 14:

(i) SEQUENCE CHARACTERISTICS:
        (A) LENGTH: 471 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: mat peptide
        (B) LOCATION: 1..471
        (C) IDENTIFICATION METHOD: S (xi) SEQUENCE DESCRIPTION: SEQ ID NO: 14:

```
TAC TTT GGC AAG CTT GAA TCT AAA TTA TCA GTC ATA AGA AAT TTG AAT       48
Tyr Phe Gly Lys Leu Glu Ser Lys Leu Ser Val Ile Arg Asn Leu Asn
1               5                   10                  15

GAC CAA GTT CTC TTC ATT GAC CAA GGA AAT CGG CCT CTA TTT GAA GAT       96
Asp Gln Val Leu Phe Ile Asp Gln Gly Asn Arg Pro Leu Phe Glu Asp
            20                  25                  30

ATG ACT GAT TCT GAC TCT AGA GAT AAT GCA CCC CGG ACC ATA TTT ATT      144
Met Thr Asp Ser Asp Ser Arg Asp Asn Ala Pro Arg Thr Ile Phe Ile
        35                  40                  45

ATA AGT ATG TAT AAA GAT AGC CAG CCT AGA GGT ATG GCT GTA ACT ATC      192
Ile Ser Met Tyr Lys Asp Ser Gln Pro Arg Gly Met Ala Val Thr Ile
    50                  55                  60

TCT GTG AAG TCT GAG AAA ATT TCA ACT CTC TCC GCT GAG AAC AAA ATT      240
Ser Val Lys Ser Glu Lys Ile Ser Thr Leu Ser Ala Glu Asn Lys Ile
65                  70                  75                  80

ATT TCC TTT AAG GAA ATG AAT CCT CCT GAT AAC ATC AAG GAT ACA AAA      288
Ile Ser Phe Lys Glu Met Asn Pro Pro Asp Asn Ile Lys Asp Thr Lys
```

```
                85                   90                   95
AGT GAC ATC ATA TTC TTT CAG AGA AGT GTC CCA GGA CAT GAT AAT AAG        336
Ser Asp Ile Ile Phe Phe Gln Arg Ser Val Pro Gly His Asp Asn Lys
            100                 105                 110

ATG CAA TTT GAA TCT TCA TCA TAC GAA GGA TAC TTT CTA GCT TGT GAA        384
Met Gln Phe Glu Ser Ser Ser Tyr Glu Gly Tyr Phe Leu Ala Cys Glu
        115                 120                 125

AAA GAG AGA GAC CTT TTT AAA CTC ATT TTG AAA AAA GAG GAT GAA TTG        432
Lys Glu Arg Asp Leu Phe Lys Leu Ile Leu Lys Lys Glu Asp Glu Leu
    130                 135                 140

GGG GAT AGA TCT ATA ATG TTC ACT GTT CAA AAC GAA GAC                    471
Gly Asp Arg Ser Ile Met Phe Thr Val Gln Asn Glu Asp
145                 150                 155
```

(2) INFORMATION FOR SEQ ID NO: 15:

(i) SEQUENCE CHARACTERISTICS:
      (A) LENGTH: 10 amino acids
      (B) TYPE: amino acid
      (D) TOPOLOGY: linear (ii) MOLECULE TYPE: peptide (v) FRAGMENT TYPE: N-terminal fragment (xi) SEQUENCE DESCRIPTION: SEQ ID NO: 15:

```
Tyr Phe Gly Lys Leu Glu Ser Lys Leu Ser
1               5                   10
```

(2) INFORMATION FOR SEQ ID NO: 16:

(i) SEQUENCE CHARACTERISTICS:
      (A) LENGTH: 471 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: mat peptide
      (B) LOCATION: 1..471
      (C) IDENTIFICATION METHOD: S (xi) SEQUENCE DESCRIPTION: SEQ ID NO: 16:

```
TAC TTT GGC AAG CTT GAA TCT AAA TTA TCA GTC ATA AGA AAT TTG AAT         48
Tyr Phe Gly Lys Leu Glu Ser Lys Leu Ser Val Ile Arg Asn Leu Asn
1               5                   10                  15

GAC CAA GTT CTC TTC ATT GAC CAA GGA AAT CGG CCT CTA TTT GAA GAT         96
Asp Gln Val Leu Phe Ile Asp Gln Gly Asn Arg Pro Leu Phe Glu Asp
            20                  25                  30

ATG ACT GAT TCT GAC TCT AGA GAT AAT GCA CCC CGG ACC ATA TTT ATT        144
Met Thr Asp Ser Asp Ser Arg Asp Asn Ala Pro Arg Thr Ile Phe Ile
        35                  40                  45

ATA AGT ATG TAT AAA GAT AGC CAG CCT AGA GGT ATG GCT GTA ACT ATC        192
Ile Ser Met Tyr Lys Asp Ser Gln Pro Arg Gly Met Ala Val Thr Ile
    50                  55                  60

TCT GTG AAG TCT GAG AAA ATT TCA ACT CTC TCC GCT GAG AAC AAA ATT        240
Ser Val Lys Ser Glu Lys Ile Ser Thr Leu Ser Ala Glu Asn Lys Ile
65                  70                  75                  80

ATT TCC TTT AAG GAA ATG AAT CCT CCT GAT AAC ATC AAG GAT ACA AAA        288
Ile Ser Phe Lys Glu Met Asn Pro Pro Asp Asn Ile Lys Asp Thr Lys
            85                  90                  95

AGT GAC ATC ATA TTC TTT CAG AGA AGT GTC CCA GGA CAT GAT AAT AAG        336
Ser Asp Ile Ile Phe Phe Gln Arg Ser Val Pro Gly His Asp Asn Lys
```

-continued

```
                100                     105                     110
ATG CAA TTT GAA TCT TCA TCA TAC GAA GGA TAC TTT CTA GCT TCT GAA     384
Met Gln Phe Glu Ser Ser Ser Tyr Glu Gly Tyr Phe Leu Ala Ser Glu
        115                     120                     125

AAA GAG AGA GAC CTT TTT AAA CTC ATT TTG AAA AAA GAG GAT GAA TTG     432
Lys Glu Arg Asp Leu Phe Lys Leu Ile Leu Lys Lys Glu Asp Glu Leu
        130                     135                     140

GGG GAT AGA TCT ATA ATG TTC ACT GTT CAA AAC GAA GAC                 471
Gly Asp Arg Ser Ile Met Phe Thr Val Gln Asn Glu Asp
145                     150                     155
```

(2) INFORMATION FOR SEQ ID NO: 17:

(i) SEQUENCE CHARACTERISTICS:
        (A) LENGTH: 11464 base pairs
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: human
        (G) CELL TYPE: placenta (ix) FEATURE:
        (A) NAME/KEY: leader peptide
        (B) LOCATION: 1..3
        (C) IDENTIFICATION METHOD: E (xi) SEQUENCE DESCRIPTION: SEQ ID NO: 17:

```
AAG ATG GCT GCT GAA CCA GTA GAA GAC AAT TGC ATC AAC TTT GTG GCA     48
    Met Ala Ala Glu Pro Val Glu Asp Asn Cys Ile Asn Phe Val Ala
        -35                     -30                     -25

ATG AAA TTT ATT GAC AAT ACG CTT TAC TTT ATA G   GTAAGG CTAATGCCAT   98
Met Lys Phe Ile Asp Asn Thr Leu Tyr Phe Ile Ala
-20                     -15                     -10

AGAACAAATA CCAGGTTCAG ATAAATCTAT TCAATTAGAA AAGATGTTGT GAGGTGAACT    158

ATTAAGTGAC TCTTTGTGTC ACCAAATTTC ACTGTAATAT TAATGGCTCT TAAAAAAATA    218

GTGGACCTCT AGAAATTAAC CACAACATGT CCAAGGTCTC AGCACCTTGT CACACCACGT    278

GTCCTGGCAC TTTAATCAGC AGTAGCTCAC TCTCCAGTTG GCAGTAAGTG CACATCATGA    338

AAATCCCAGT TTTCATGGGA AAATCCCAGT TTTCATTGGA TTTCCATGGG AAAAATCCCA    398

GTACAAAACT GGGTGCATTC AGGAAATACA ATTTCCCAAA GCAAATTGGC AAATTATGTA    458

AGAGATTCTC TAAATTTAGA GTTCCGTGAA TTACACCATT TTATGTAAAT ATGTTTGACA    518

AGTAAAAATT GATTCTTTTT TTTTTTTTCT GTTGCCCAGG CTGGAGTGCA GTGGCACAAT    578

CTCTGCTCAC TGCAACCTCC ACCTCCTGGG TTCAAGCAAT TCTCCTGCCT CAGCCTTCTG    638

AGTAGCTGGG ACTACAGGTG CATCCCGCCA TGCCTGGCTA ATTTTTGGGT ATTTTTACTA    698

GAGACAGGGT TTTGGCATGT TGTCCAGGCT GGTCTTGGAC TCCTGATCTC AGATGATCCT    758

CCTGGCTCGG GCTCCCAAAG TGCTGGGATT ACAGGCATGA ACCACCACAC ATGGCCTAAA    818

AATTGATTCT TATGATTAAT CTCCTGTGAA CAATTTGGCT TCATTTGAAA GTTTGCCTTC    878

ATTTGAAACC TTCATTTAAA AGCCTGAGCA ACAAAGTGAG ACCCCATCTC TACAAAAAAC    938

TGCAAAATAT CCTGTGGACA CCTCCTACCT TCTGTGGAGG CTGAAGCAGG AGGATCACTT    998

GAGCCTAGGA ATTTGAGCCT GCAGTGAGCT ATGATCCCAC CCTACACTC AGCCTGCAT     1058

GACAGTAGAC CCTGACACAC ACACACAAAA AAAAACCTTC ATAAAAAATT ATTAGTTGAC    1118

TTTTCTTAGG TGACTTTCCG TTTAAGCAAT AAATTTAAAA GTAAATCTC TAATTTTAGA     1178
```

| | |
|---|---|
| AAATTTATTT TTAGTTACAT ATTGAAATTT TTAAACCCTA GGTTTAAGTT TTATGTCTAA | 1238 |
| ATTACCTGAG AACACACTAA GTCTGATAAG CTTCATTTTA TGGGCCTTTT GGATGATTAT | 1298 |
| ATAATATTCT GATGAAAGCC AAGACAGACC CTTAAACCAT AAAAATAGGA GTTCGAGAAA | 1358 |
| GAGGAGTAGC AAAAGTAAAA GCTAGAATGA GATTGAATTC TGAGTCGAAA TACAAAATTT | 1418 |
| TACATATTCT GTTTCTCTCT TTTTCCCCCT CTTAG    CT GAA GAT GAT G    GTAAA<br>                                                                                       Ala Glu Asp Asp Glu<br>                                                                                       -10 | 1470 |
| GTAGAAATGA ATTTATTTTT CTTTGCAAAC TAAGTATCTG CTTGAGACAC ATCTATCTCA | 1530 |
| CCATTGTCAG CTGAGGAAAA AAAAAAATGG TTCTCATGCT ACCAATCTGC CTTCAAAGAA | 1590 |
| ATGTGGACTC AGTAGCACAG CTTTGGAATG AAGATGATCA TAAGAGATAC AAAGAAGAAC | 1650 |
| CTCTAGCAAA AGATGCTTCT CTATGCCTTA AAAAATTCTC CAGCTCTTAG AATCTACAAA | 1710 |
| ATAGACTTTG CCTGTTTCAT TGGTCCTAAG ATTAGCATGA AGCCATGGAT TCTGTTGTAG | 1770 |
| GGGGAGCGTT GCATAGGAAA AAGGGATTGA AGCATTAGAA TTGTCCAAAA TCAGTAACAC | 1830 |
| CTCCTCTCAG AAATGCTTTG GAAGAAGCC TGGAAGGTTC CGGGTTGGTG GTGGGGTGGG | 1890 |
| GCAGAAAATT CTGGAAGTAG AGGAGATAGG AATGGGTGGG GCAAGAAGAC CACATTCAGA | 1950 |
| GGCCAAAAGC TGAAAGAAAC CATGGCATTT ATGATGAATT CAGGGTAATT CAGAATGGAA | 2010 |
| GTAGAGTAGG AGTAGGAGAC TGGTGAGAGG AGCTAGAGTG ATAAACAGGG TGTAGAGCAA | 2070 |
| GACGTTCTCT CACCCCAAGA TGTGAAATTT GGACTTTATC TTGGAGATAA TAGGGTTAAT | 2130 |
| TAAGCACAAT ATGTATTAGC TAGGGTAAAG ATTAGTTTGT TGTAACAAAG ACATCCAAAG | 2190 |
| ATACAGTAGC TGAATAAGAT AGAGAATTTT TCTCTCAAAG AAAGTCTAAG TAGGCAGCTC | 2250 |
| AGAAGTAGTA TGGCTGGAAG CAACCTGATG ATATTGGGAC CCCCAACCTT CTTCAGTCTT | 2310 |
| GTACCCATCA TCCCCTAGTT GTTGATCTCA CTCACATAGT TGAAAATCAT CATACTTCCT | 2370 |
| GGGTTCATAT CCCAGTTATC AAGAAAGGGT CAAGAGAAGT CAGGCTCATT CCTTTCAAAG | 2430 |
| ACTCTAATTG GAAGTTAAAC ACATCAATCC CCCTCATATT CCATTGACTA GAATTTAATC | 2490 |
| ACATGGCCAC ACCAAGTGCA AGGAAATCTG GAAAATATAA TCTTTATTCC AGGTAGCCAT | 2550 |
| ATGACTCTTT AAAATTCAGA AATAATATAT TTTTAAAATA TCATTCTGGC TTTGGTATAA | 2610 |
| AGAATTGATG GTGTGGGGTG AGGAGGCCAA AATTAAGGGT TGAGAGCCTA TTATTTTAGT | 2670 |
| TATTACAAGA AATGATGGTG TCATGAATTA AGGTAGACAT AGGGGAGTGC TGATGAGGAG | 2730 |
| CTGTGAATGG ATTTTAGAAA CACTTGAGAG AATCAATAGG ACATGATTTA GGGTTGGATT | 2790 |
| TGGAAAGGAG AAGAAAGTAG AAAAGATGAT GCCTACATTT TTCACTTAGG CAATTTGTAC | 2850 |
| CATTCAGTGA AATAGGGAAC ACAGGAGGAA GAGCAGGTTT TGGTGTATAC AAAGAGGAGG | 2910 |
| ATGGATGACG CATTTCGTTT TGGATCTGAG ATGTCTGTGG AACGTCCTAG TGGAGATGTC | 2970 |
| CACAAACTCT TCTACATGTG GTTCTGAGTT CAGGACACAG ATTTGGGCTG AGATAGAGA | 3030 |
| TATTGTAGGC TTATACATAG AAATGGCATT TGAATCTATA GAGATAAAAA GACACATCAG | 3090 |
| AGGAAATGTG TAAAGTGAGA GAGGAAAAGC CAAGTACTGT GCTGGGGGGA ATACCTACAT | 3150 |
| TTAAAGGATG CAGTAGAAAG AAGCTAATAA ACAACAGAGA GCAGACTAAC CAAAAGGGGA | 3210 |
| GAAGAAAAAC CAAGAGAATT CCACCGACTC CCAGGAGAGC ATTTCAAGAT TGAGGGGATA | 3270 |
| GGTGTTGTGT TGAATTTTGC AGCCTTGAGA ATCAAGGGCC AGAACACAGC TTTTAGATTT | 3330 |
| AGCAACAAGG AGTTTGGTGA TCTCAGTGAA AGCAGCTTGA TGGTGAAATG GAGGCAGAGG | 3390 |
| CAGATTGCAA TGAGTGAAAC AGTGAATGGG AAGTGAAGAA ATGATACAGA TAATTCTTGC | 3450 |

```
TAAAAGCTTG GCTGTTAAAA GGAGGAGAGA AACAAGACTA GCTGCAAAGT GAGATTGGGT    3510

TGATGGAGCA GTTTTAAATC TCAAAATAAA GAGCTTTGTG CTTTTTTGAT TATGAAAATA    3570

ATGTGTTAAT TGTAACTAAT TGAGGCAATG AAAAAGATA ATAATATGAA AGATAAAAAT     3630

ATAAAAACCA CCCAGAAATA ATGATAGCTA CCATTTTGAT ACAATATTTC TACACTCCTT    3690

TCTATGTATA TATACAGACA CAGAAATGCT TATATTTTTA TTAAAAGGGA TTGTACTATA    3750

CCTAAGCTGC TTTTTCTAGT TAGTGATATA TATGGACATC TCTCCATGGC AACGAGTAAT    3810

TGCAGTTATA TTAAGTTCAT GATATTTCAC AATAAGGGCA TATCTTTGCC CTTTTTATTT    3870

AATCAATTCT TAATTGGTGA ATGTTTGTTT CCAGTTTGTT GTTGTTATTA ACAATGTTCC    3930

CATAAGCATT CCTGTACACC AATGTTCACA CATTTGTCTG ATTTTTTCTT CAGGATAAAA    3990

CCCAGGAGGT AGAATTGCTG GGTTGATAGA AGAGAAAGGA TGATTGCCAA ATTAAAGCTT    4050

CAGTAGAGGG TACATGCCGA GCACAAATGG GATCAGCCCT AGATACCAGA ATGGCACTT     4110

TCTCATTTCC CCTTGGGACA AAAGGGAGAG AGGCAATAAC TGTGCTGCCA GAGTTAAATT    4170

TGTACGTGGA GTAGCAGGAA ATCATTTGCT GAAAATGAAA ACAGAGATGA TGTTGTAGAG    4230

GTCCTGAAGA GAGCAAAGAA AATTTGAAAT TGCGGCTATC AGCTATGAAA GAGAGTGCTG    4290

AACTGGAAAA CAAAAGAAGT ATTGACAATT GGTATGCTTG TAATGGCACC GATTTGAACG    4350

CTTGTGCCAT TGTTCACCAG CAGCACTCAG CAGCCAAGTT TGGAGTTTTG TAGCAGAAAG    4410

ACAAATAAGT TAGGGATTTA ATATCCTGGC CAAATGGTAG ACAAAATGAA CTCTGAGATC    4470

CAGCTGCACA GGGAAGGAAG GGAAGACGGG AAGAGGTTAG ATAGGAAATA CAAGAGTCAG    4530

GAGACTGGAA GATGTTGTGA TATTTAAGAA CACATAGAGT TGGAGTAAAA GTGTAAGAAA    4590

ACTAGAAGGG TAAGAGACCG GTCAGAAAGT AGGCTATTTG AAGTTAACAC TTCAGAGGCA    4650

GAGTAGTTCT GAATGGTAAC AAGAAATTGA GTGTGCCTTT GAGAGTAGGT TAAAAAACAA    4710

TAGGCAACTT TATTGTAGCT ACTTCTGGAA CAGAAGATTG TCATTAATAG TTTTAGAAAA    4770

CTAAAATATA TAGCATACTT ATTTGTCAAT TAACAAAGAA ACTATGTATT TTTAAATGAG    4830

ATTTAATGTT TATTGTAG  AA AAC CTG GAA TCA GAT TAC TTT GGC AAG CTT    4880
                    Glu Asn Leu Glu Ser Asp Tyr Phe Gly Lys Leu
                         -5                  1                5

GAA TCT AAA TTA TCA GTC ATA AGA AAT TTG AAT GAC CAA GTT CTC TTC    4928
Glu Ser Lys Leu Ser Val Ile Arg Asn Leu Asn Asp Gln Val Leu Phe
             10                  15                  20

ATT GAC CAA GGA AAT CGG CCT CTA TTT GAA GAT ATG ACT GAT TCT GAC    4976
Ile Asp Gln Gly Asn Arg Pro Leu Phe Glu Asp Met Thr Asp Ser Asp
             25                  30                  35

TGT AGA G   GTATTTTTT TTAATTCGCA AACATAGAAA TGACTAGCTA CTTCTTCCCA    5032
Cys Arg Asp
        40

TTCTGTTTTA CTGCTTACAT TGTTCCGTGC TAGTCCCAAT CCTCAGATGA AAAGTCACAG    5092

GAGTGACAAT AATTTCACTT ACAGGAAACT TTATAAGGCA TCCACGTTTT TTAGTTGGGG    5152

TAAAAAATTG GATACAATAA GACATTGCTA GGGGTCATGC CTCTCTGAGC CTGCCTTTGA    5212

ATCACCAATC CCTTTATTGT GATTGCATTA ACTGTTAAA ACCTCTATAG TTGGATGCTT     5272

AATCCCTGCT TGTTACAGCT GAAAATGCTG ATAGTTTACC AGGTGTGGTG GCATCTATCT    5332

GTAATCCTAG CTACTTGGGA GGCTCAAGCA GGAGGATTGC TTGAGGCCAG ACTTTGAGG     5392

CTGTAGTACA CTGTGATCGT ACCTGTGAAT AGCCACTGCA CTCCAGCCTG GGTGATATAC    5452

AGACCTTGTC TCTAAAATTA AAAAAAAAA AAAAAAAAC CTTAGGAAAG GAAATTGATC      5512

AAGTCTACTG TGCCTTCCAA AACATGAATT CCAAATATCA AAGTTAGGCT GAGTTGAAGC    5572
```

```
AGTGAATGTG CATTCTTTAA AAATACTGAA TACTTACCTT AACATATATT TTAAATATTT    5632

TATTTAGCAT TTAAAAGTTA AAAACAATCT TTTAGAATTC ATATCTTTAA AATACTCAAA    5692

AAAGTTGCAG CGTGTGTGTT GTAATACACA TTAAACTGTG GGGTTGTTTG TTTGTTTGAG    5752

ATGCAGTTTC ACTCTGTCAC CCAGGCTGAA GTGCAGTGCA GTGCAGTGGT GTGATCTCGG    5812

CTCACTACAA CCTCCACCTC CCACGTTCAA GCGATTCTCA TGCCTCAGTC TCCCGAGTAG    5872

GTGGGATTAC AGGCATGCAC CACTTACACC CGGCTAATTT TTGTATTTTT AGTAGAGCTG    5932

GGGTTTCACC ATGTTGGCCA GGCTGGTCTC AAACCCCTAA CCTCAAGTGA TCTGCCTGCC    5992

TCAGCCTCCC AAACAAACAA ACAACCCCAC AGTTTAATAT GTGTTACAAC ACACATGCTG    6052

CAACTTTTAT GAGTATTTTA ATGATATAGA TTATAAAAGG TTGTTTTTAA CTTTTAAATG    6112

CTGGGATTAC AGGCATGAGC CACTGTGCCA GGCCTGAACT GTGTTTTTAA AAATGTCTGA    6172

CCAGCTGTAC ATAGTCTCCT GCAGACTGGC CAAGTCTCAA AGTGGGAACA GGTGTATTAA    6232

GGACTATCCT TTGGTTAAAT TTCCGCAAAT GTTCCTGTGC AAGAATTCTT CTAACTAGAG    6292

TTCTCATTTA TTATATTTAT TTCAG  AT AAT GCA CCC CGG ACC ATA TTT ATT       6343
                              Asp Asn Ala Pro Arg Thr Ile Phe Ile
                                  40              45

ATA AGT ATG TAT AAA GAT AGC CAG CCT AGA GGT ATG GCT GTA ACT ATC      6391
Ile Ser Met Tyr Lys Asp Ser Gln Pro Arg Gly Met Ala Val Thr Ile
 50                  55                  60

TCT GTG AAG TGT GAG AAA ATT TCA ACT CTC TCC TGT GAG AAC AAA ATT      6439
Ser Val Lys Cys Glu Lys Ile Ser Thr Leu Ser Cys Glu Asn Lys Ile
65                  70                  75                  80

ATT TCC TTT AAG GTAAG ACTGAGCCTT ACTTTGTTTT CAATCATGTT AATATAATCA    6496
Ile Ser Phe Lys
ATATAATTAG AAATATAACA TTATTTCTAA TGTTAATATA AGTAATGTAA TTAGAAAACT    6556

CAAATATCCT CAGACCAACC TTTTGTCTAG AACAGAAATA ACAAGAAGCA GAGAACCATT    6616

AAAGTGAATA CTTACTAAAA ATTATCAAAC TCTTTACCTA TTGTGATAAT GATGGTTTTT    6676

CTGAGCCTGT CACAGGGGAA GAGGAGATAC AACACTTGTT TTATGACCTG CATCTCCTGA    6736

ACAATCAGTC TTTATACAAA TAATAATGTA GAATACATAT GTGAGTTATA CATTTAAGAA    6796

TAACATGTGA CTTTCCAGAA TGAGTTCTGC TATGAAGAAT GAAGCTAATT ATCCTTCTAT    6856

ATTTCTACAC CTTTGTAAAT TATGATAATA TTTTAATCCC TAGTTGTTTT GTTGCTGATC    6916

CTTAGCCTAA GTCTTAGACA CAAGCTTCAG CTTCCAGTTG ATGTATGTTA TTTTTAATGT    6976

TAATCTAATT GAATAAAAGT TATGAGATCA GCTGTAAAAG TAATGCTATA ATTATCTTCA    7036

AGCCAGGTAT AAAGTATTTC TGGCCTCTAC TTTTTCTCTA TTATTCTCCA TTATTATTCT    7096

CTATTATTTT TCTCTATTTC CTCCATTATT GTTAGATAAA CCACAATTAA CTATAGCTAC    7156

AGACTGAGCC AGTAAGAGTA GCCAGGGATG CTTACAAATT GGCAATGCTT CAGAGGAGAA    7216

TTCCATGTCA TGAAGACTCT TTTTGAGTGG AGATTTGCCA ATAAATATCC GCTTTCATGC    7276

CCACCCAGTC CCCACTGAAA GACAGTTAGG ATATGACCTT AGTGAAGGTA CCAAGGGGCA    7336

ACTTGGTAGG GAGAAAAAAG CCACTCTAAA ATATAATCCA AGTAAGAACA GTGCATATGC    7396

AACAGATACA GCCCCCAGAC AAATCCCTCA GCTATCTCCC TCCAACCAGA GTGCCACCCC    7456

TTCAGGTGAC AATTTGGAGT CCCCATTCTA GACCTGACAG GCAGCTTAGT TATCAAAATA    7516

GCATAAGAGG CCTGGGATGG AAGGGTAGGG TGGAAAGGGT TAAGCATGCT GTTACTGAAC    7576

AACATAATTA GAAGGGAAGG AGATGGCCAA GCTCAAGCTA TGTGGGATAG AGGAAAACTC    7636

AGCTGCAGAG GCAGATTCAG AAACTGGGAT AAGTCCGAAC CTACAGGTGG ATTCTTGTTG    7696
```

```
AGGGAGACTG GTGAAAATGT TAAGAAGATG GAAATAATGC TTGGCACTTA GTAGGAACTG    7756

GGCAAATCCA TATTTGGGGG AGCCTGAAGT TTATTCAATT TTGATGGCCC TTTTAAATAA    7816

AAAGAATGTG GCTGGGCGTG GTGGCTCACA CCTGTAATCC CAGCACTTTG GGAGGCCGAG    7876

GGGGGCGGAT CACCTGAAGT CAGGAGTTCA AGACCAGCCT GACCAACATG GAGAAACCCC    7936

ATCTCTACTA AAAATACAAA ATTAGCTGGG CGTGGTGGCA TATGCCTGTA ATCCCAGCTA    7996

CTCGGGAGGC TGAGGCAGGA GAATCTTTTG AACCCGGGAG GCAGAGGTTG CGATGAGCCT    8056

AGATCGTGCC ATTGCACTCC AGCCTGGGCA CAAGAGCAA AACTCGGTCT CAAAAAAAAA    8116

AAAAAAAAAG TGAAATTAAC CAAAGGCATT AGCTTAATAA TTTAATACTG TTTTTAAGTA    8176

GGGCGGGGGG TGGCTGGAAG AGATCTGTGT AAATGAGGGA ATCTGACATT TAAGCTTCAT    8236

CAGCATCATA GCAAATCTGC TTCTGGAAGG AACTCAATAA ATATTAGTTG GAGGGGGGGA    8296

GAGAGTGAGG GGTGGACTAG GACCAGTTTT AGCCCTTGTC TTTAATCCCT TTTCCTGCCA    8356

CTAATAAGGA TCTTAGCAGT GGTTATAAAA GTGGCCTAGG TTCTAGATAA TAAGATACAA    8416

CAGGCCAGGC ACAGTGGCTC ATGCCTATAA TCCCAGCACT TTGGGAGGGC AAGGCGAGTG    8476

TCTCACTTGA GATCAGGAGT TCAAGACCAG CCTGGCCAGC ATGGCGATAC TCTGTCTCTA    8536

CTAAAAAAAA TACAAAAATT AGCCAGGCAT GGTGGCATGC ACCTGTAATC CCAGCTACTC    8596

GTGAGCCTGA GGCAGAAGAA TCGCTTGAAA CCAGGAGGTG TAGGCTGCAG TGAGCTGAGA    8656

TCGCACCACT GCACTCCAGC CTGGGCGACA GAATGAGACT TTGTCTCAAA AAAGAAAAA    8716

GATACAACAG GCTACCCTTA TGTGCTCACC TTTCACTGTT GATTACTAGC TATAAAGTCC    8776

TATAAAGTTC TTTGGTCAAG AACCTTGACA ACACTAAGAG GGATTTGCTT TGAGAGGTTA    8836

CTGTCAGAGT CTGTTTCATA TATATACATA TACATGTATA TATGTATCTA TATCCAGGCT    8896

TGGCCAGGGT TCCCTCAGAC TTTCCAGTGC ACTTGGGAGA TGTTAGGTCA ATATCAACTT    8956

TCCCTGGATT CAGATTCAAC CCCTTCTGAT GTAAAAAAAA AAAAAAAAAA GAAAGAAATC    9016

CCTTTCCCCT TGGAGCACTC AAGTTTCACC AGGTGGGGCT TTCCAAGTTG GGGGTTCTCC    9076

AAGGTCATTG GGATTGCTTT CACATCCATT TGCTATGTAC CTTCCCTATG ATGGCTGGGA    9136

GTGGTCAACA TCAAAACTAG GAAAGCTACT GCCCAAGGAT GTCCTTACCT CTATTCTGAA    9196

ATGTGCAATA AGTGTGATTA AAGAGATTGC CTGTTCTACC TATCCACACT CTCGCTTTCA    9256

ACTGTAACTT TCTTTTTTTC TTTTTTTCTT TTTTTCTTTT TTTTGAAAC GGAGTCTCGC    9316

TCTGTCGCCC AGGCTAGAGT GCAGTGGCAC GATCTCAGCT CACTGCAAGC TCTGCCTCCC    9376

GGGTTCACGC CATTCTCCTG CCTCACCCTC CCAAGCAGCT GGGACTACAG GCGCCTGCCA    9436

CCATGCCCAG CTAATTTTTT GTATTTTTAG TAGAGACGGG GTTTCACCGT GTTAGCCAGG    9496

ATGGTCTCGA TCTCCTGAAC TTGTGATCCG CCCGCCTCAG CCTCCCAAAG TGCTGGGATT    9556

ACAGGCGTGA GCCATCGCAC CCGGCTCAAC TGTAACTTTC TATACTGGTT CATCTTCCCC    9616

TGTAATGTTA CTAGAGCTTT TGAAGTTTTG GCTATGGATT ATTTCTCATT TATACATTAG    9676

ATTTCAGATT AGTTCCAAAT TGATGCCCAC AGCTTAGGGT CTCTTCCTAA ATTGTATATT    9736

GTAGACAGCT GCAGAAGTGG GTGCCAATAG GGGAACTAGT TTATACTTTC ATCAACTTAG    9796

GACCCACACT TGTTGATAAA GAACAAAGGT CAAGAGTTAT GACTACTGAT TCCACAACTG    9856

ATTGAGAAGT TGGAGATAAC CCCGTGACCT CTGCCATCCA GAGTCTTTCA GGCATCTTTG    9916

AAGGATGAAG AAATGCTATT TTAATTTTGG AGGTTTCTCT ATCAGTGCTT AGGATCATGG    9976

GAATCTGTGC TGCCATGAGG CCAAAATTAA GTCCAAAACA TCTACTGGTT CCAGGATTAA    10036

CATGGAAGAA CCTTAGGTGG TGCCCACATG TTCTGATCCA TCCTGCAAAA TAGACATGCT    10096
```

```
GCACTAACAG GAAAAGTGCA GGCAGCACTA CCAGTTGGAT AACCTGCAAG ATTATAGTTT    10156

CAAGTAATCT AACCATTTCT CACAAGGCCC TATTCTGTGA CTGAAACATA CAAGAATCTG    10216

CATTTGGCCT TCTAAGGCAG GGCCCAGCCA AGGAGACCAT ATTCAGGACA GAAATTCAAG    10276

ACTACTATGG AACTGGAGTG CTTGGCAGGG AAGACAGAGT CAAGGACTGC CAACTGAGCC    10336

AATACAGCAG GCTTACACAG GAACCCAGGG CCTAGCCCTA CAACAATTAT TGGGTCTATT    10396

CACTGTAAGT TTTAATTTCA GGCTCCACTG AAAGAGTAAG CTAAGATTCC TGGCACTTTC    10456

TGTCTCTCTC ACAGTTGGCT CAGAAATGAG AACTGGTCAG GCCAGGCATG GTGGCTTACA    10516

CCTGGAATCC CAGCACTTTG GGAGGCCGAA GTGGGAGGGT CACTTGAGGC CAGGAGTTCA    10576

GGACCAGCTT AGGCAACAAA GTGAGATACC CCCTGACCCC TTCTCTACAA AAATAAATTT    10636

TAAAAATTAG CCAAATGTGG TGGTGTATAC TTACAGTCCC AGCTACTCAG GAGGCTGAGG    10696

CAGGGGGATT GCTTGAGCCC AGGAATTCAA GGCTGCAGTG AGCTATGATT TCACCACTGC    10756

ACTTCTGGCT GGGCAACAGA GCGAGACCCT GTCTCAAAGC AAAAGAAAA  AGAAACTAGA    10816

ACTAGCCTAA GTTTGTGGGA GGAGGTCATC ATCGTCTTTA GCCGTGAATG GTTATTATAG    10876

AGGACAGAAA TTGACATTAG CCCAAAAAGC TTGTGGTCTT TGCTGGAACT CTACTTAATC    10936

TTGAGCAAAT GTGGACACCA CTCAATGGGA GAGGAGAGAA GTAAGCTGTT TGATGTATAG    10996

GGGAAAACTA GAGGCCTGGA ACTGAATATG CATCCCATGA CAGGGAGAAT AGGAGATTCG    11056

GAGTTAAGAA GGAGAGGAGG TCAGTACTGC TGTTCAGAGA TTTTTTTTAT GTAACTCTTG    11116

AGAAGCAAAA CTACTTTTGT TCTGTTTGGT AATATACTTC AAAACAAACT TCATATATTC    11176

AAATTGTTCA TGTCCTGAAA TAATTAGGTA ATGTTTTTTT CTCTATAG GAA ATG AAT       11233
                                                    Glu Met Asn
                                                             85

CCT CCT GAT AAC ATC AAG GAT ACA AAA AGT GAC ATA ATA TTC TTT CAG         11281
Pro Pro Asp Asn Ile Lys Asp Thr Lys Ser Asp Ile Ile Phe Phe Glu
        90                  95                 100

AGA AGT GTC CCA GGA CAT GAT AAT AAG ATG CAA TTT GAA TCT TCA TCA         11329
Arg Ser Val Pro Gly His Asp Asn Lys Met Gln Phe Glu Ser Ser Ser
    105                 110                 115

TAC GAA GGA TAC TTT CTA GCT TGT GAA AAA GAG AGA GAC CTT TTT AAA         11377
Tyr Glu Gly Tyr Phe Leu Ala Cys Glu Lys Glu Arg Asp Leu Phe Lys
120                 125                 130                 135

CTC ATT TTG AAA AAA GAG GAT GAA TTG GGG GAT AGA TCT ATA ATG TTC         11425
Leu Ile Leu Lys Lys Glu Asp Glu Leu Gly Asp Arg Ser Ile Met Phe
            140                 145                 150

ACT GTT CAA AAC GAA GAC TAGCTATTAA AATTTCATGC C                         11464
Thr Val Gln Asn Glu Asp
            155

(2) INFORMATION FOR SEQ ID NO: 18:

(i) SEQUENCE CHARACTERISTICS:
        (A) LENGTH: 471 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: mouse
        (G) CELL TYPE: liver (ix) FEATURE:
        (A) NAME/KEY: mat peptide
        (B) LOCATION: 1..471
```

(C) IDENTIFICATION METHOD: S (xi) SEQUENCE DESCRIPTION: SEQ ID NO: 18:

| | | | | | | | | | | | | | | | | |
|---|---|---|---|---|---|---|---|---|---|---|---|---|---|---|---|---|
| AAC | TTT | GGC | CGA | CTT | CAC | TGT | ACA | ACC | GCA | GTA | ATA | CGG | AAT | ATA | AAT | 48 |
| Asn | Phe | Gly | Arg | Leu | His | Cys | Thr | Thr | Ala | Val | Ile | Arg | Asn | Ile | Asn | |
| 1 | | | 5 | | | | 10 | | | | | 15 | | | | |
| GAC | CAA | GTT | CTC | TTC | GTT | GAC | AAA | AGA | CAG | CCT | GTG | TTC | GAG | GAT | ATG | 96 |
| Asp | Gln | Val | Leu | Phe | Val | Asp | Lys | Arg | Gln | Pro | Val | Phe | Glu | Asp | Met | |
| | | | 20 | | | | | 25 | | | | | 30 | | | |
| ACT | GAT | ATT | GAT | CAA | AGT | GCC | AGT | GAA | CCC | CAG | ACC | AGA | CTG | ATA | ATA | 144 |
| Thr | Asp | Ile | Asp | Gln | Ser | Ala | Ser | Glu | Pro | Gln | Thr | Arg | Leu | Ile | Ile | |
| | | 35 | | | | | 40 | | | | | 45 | | | | |
| TAC | ATG | TAC | AAA | GAC | AGT | GAA | GTA | AGA | GGA | CTG | GCT | GTG | ACC | CTC | TCT | 192 |
| Tyr | Met | Tyr | Lys | Asp | Ser | Glu | Val | Arg | Gly | Leu | Ala | Val | Thr | Leu | Ser | |
| 50 | | | | | 55 | | | | | 60 | | | | | | |
| GTG | AAG | GAT | AGT | AAA | ATG | TCT | ACC | CTC | TCC | TGT | AAG | AAC | AAG | ATC | ATT | 240 |
| Val | Lys | Asp | Ser | Lys | Met | Ser | Thr | Leu | Ser | Cys | Lys | Asn | Lys | Ile | Ile | |
| 65 | | | | 70 | | | | | 75 | | | | | 80 | | |
| TCC | TTT | GAG | GAA | ATG | GAT | CCA | CCT | GAA | AAT | ATT | GAT | GAT | ATA | CAA | AGT | 288 |
| Ser | Phe | Glu | Glu | Met | Asp | Pro | Pro | Glu | Asn | Ile | Asp | Asp | Ile | Gln | Ser | |
| | | | | 85 | | | | | 90 | | | | | 95 | | |
| GAT | CTC | ATA | TTC | TTT | CAG | AAA | CGT | GTT | CCA | GGA | CAC | AAC | AAG | ATG | GAG | 336 |
| Asp | Leu | Ile | Phe | Phe | Gln | Lys | Arg | Val | Pro | Gly | His | Asn | Lys | Met | Glu | |
| | | | 100 | | | | | 105 | | | | | 110 | | | |
| TTT | GAA | TCT | TCA | CTG | TAT | GAA | GGA | CAC | TTT | CTT | GCT | TGC | CAA | AAG | GAA | 384 |
| Phe | Glu | Ser | Ser | Leu | Tyr | Glu | Gly | His | Phe | Leu | Ala | Cys | Gln | Lys | Glu | |
| | | 115 | | | | | 120 | | | | | 125 | | | | |
| GAT | GAT | GCT | TTC | AAA | CTC | ATT | CTG | AAA | AAA | AAG | GAT | GAA | AAT | GGG | GAT | 432 |
| Asp | Asp | Ala | Phe | Lys | Leu | Ile | Leu | Lys | Lys | Lys | Asp | Glu | Asn | Gly | Asp | |
| | 130 | | | | | 135 | | | | | 140 | | | | | |
| AAA | TCT | GTA | ATG | TTC | ACT | CTC | ACT | AAC | TTA | CAT | CAA | AGT | | | | 471 |
| Lys | Ser | Val | Met | Phe | Thr | Leu | Thr | Asn | Leu | His | Gln | Ser | | | | |
| 145 | | | | | 150 | | | | | 155 | | | | | | |

(2) INFORMATION FOR SEQ ID NO: 19:

(i) SEQUENCE CHARACTERISTICS:
    (A) LENGTH: 9 amino acids
    (B) TYPE: amino acid
    (D) TOPOLOGY: linear (ii) MOLECULE TYPE: peptide (v) FRAGMENT TYPE: N-terminal fragment (xi) SEQUENCE DESCRIPTION: SEQ ID NO: 19:

Asn Phe Gly Arg Leu His Cys Thr Thr
1               5

(2) INFORMATION FOR SEQ ID NO: 20:

(i) SEQUENCE CHARACTERISTICS:
    (A) LENGTH: 157 amino acids
    (B) TYPE: amino acid
    (D) TOPOLOGY: linear (ii) MOLECULE TYPE: peptide (xi) SEQUENCE DESCRIPTION: SEQ ID NO: 20:

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
                20                  25                  30

```
Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
 50                  55                  60

Ser Val Lys Ser Glu Lys Ile Ser Thr Leu Ser Cys Glu Asn Lys Ile
 65                  70                  75                  80

Ile Ser Phe Lys Glu Met Asn Pro Pro Asp Asn Ile Lys Asp Thr Lys
                 85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
                115                 120                 125

Lys Glu Arg Asp Leu Phe Lys Leu Ile Leu Lys Lys Glu Asp Glu Leu
        130                 135                 140

Gly Asp Arg Ser Ile Met Phe Thr Val Gln Asn Glu Asp
145                 150                 155
```

(2) INFORMATION FOR SEQ ID NO: 21:

(i) SEQUENCE CHARACTERISTICS:
        (A) LENGTH: 157 amino acids
        (B) TYPE: amino acid
        (D) TOPOLOGY: linear (ii) MOLECULE TYPE: peptide (xi) SEQUENCE DESCRIPTION: SEQ ID NO: 21:

```
Tyr Phe Gly Lys Leu Glu Ser Lys Leu Ser Val Ile Arg Asn Leu Asn
 1               5                  10                  15

Asp Gln Val Leu Phe Ile Asp Gln Gly Asn Arg Pro Leu Phe Glu Asp
         20                  25                  30

Met Thr Asp Ser Asp Ser Arg Asp Asn Ala Pro Arg Thr Ile Phe Ile
        35                  40                  45

Ile Ser Met Tyr Lys Asp Ser Gln Pro Arg Gly Met Ala Val Thr Ile
 50                  55                  60

Ser Val Lys Ser Glu Lys Ile Ser Thr Leu Ser Cys Glu Asn Lys Ile
 65                  70                  75                  80

Ile Ser Phe Lys Glu Met Asn Pro Pro Asp Asn Ile Lys Asp Thr Lys
                 85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
                115                 120                 125

Lys Glu Arg Asp Leu Phe Lys Leu Ile Leu Lys Lys Glu Asp Glu Leu
        130                 135                 140

Gly Asp Arg Ser Ile Met Phe Thr Val Gln Asn Glu Asp
145                 150                 155
```

(2) INFORMATION FOR SEQ ID NO: 22:

(i) SEQUENCE CHARACTERISTICS:
        (A) LENGTH: 157 amino acids
        (B) TYPE: amino acid
        (D) TOPOLOGY: linear (ii) MOLECULE TYPE: peptide (xi) SEQUENCE DESCRIPTION: SEQ ID NO: 22:

Tyr Phe Gly Lys Leu Glu Ser Lys Leu Ser Val Ile Arg Asn Leu Asn

```
              1               5                  10                 15
Tyr Phe Gly Lys Leu Glu Ser Lys Leu Ser Val Ile Arg Asn Leu Asn
1               5                  10                 15

Asp Gln Val Leu Phe Ile Asp Gln Gly Asn Arg Pro Leu Phe Glu Asp
            20                  25                 30

Met Thr Asp Ser Asp Cys Arg Asp Asn Ala Pro Arg Thr Ile Phe Ile
            35                  40                 45

Ile Ser Met Tyr Lys Asp Ser Gln Pro Arg Gly Met Ala Val Thr Ile
            50                  55                 60

Ser Val Lys Ser Glu Lys Ile Ser Thr Leu Ser Cys Glu Asn Lys Ile
65                  70                  75                 80

Ile Ser Phe Lys Glu Met Asn Pro Pro Asp Asn Ile Lys Asp Thr Lys
            85                  90                 95

Ser Asp Ile Ile Phe Phe Gln Arg Ser Val Pro Gly His Asp Asn Lys
            100                 105                110

Met Gln Phe Glu Ser Ser Ser Tyr Glu Gly Tyr Phe Leu Ala Ser Glu
            115                 120                125

Lys Glu Arg Asp Leu Phe Lys Leu Ile Leu Lys Lys Glu Asp Glu Leu
            130                 135                140

Gly Asp Arg Ser Ile Met Phe Thr Val Gln Asn Glu Asp
145                 150                 155
```

(2) INFORMATION FOR SEQ ID NO: 23:

(i) SEQUENCE CHARACTERISTICS:
        (A) LENGTH: 157 amino acids
        (B) TYPE: amino acid
        (D) TOPOLOGY: linear (ii) MOLECULE TYPE: peptide (xi) SEQUENCE DESCRIPTION: SEQ ID NO: 23:

```
Tyr Phe Gly Lys Leu Glu Ser Lys Leu Ser Val Ile Arg Asn Leu Asn
1               5                  10                 15

Asp Gln Val Leu Phe Ile Asp Gln Gly Asn Arg Pro Leu Phe Glu Asp
            20                  25                 30

Met Thr Asp Ser Asp Ser Arg Asp Asn Ala Pro Arg Thr Ile Phe Ile
            35                  40                 45

Ile Ser Met Tyr Lys Asp Ser Gln Pro Arg Gly Met Ala Val Thr Ile
            50                  55                 60

Ser Val Lys Ser Glu Lys Ile Ser Thr Leu Ser Cys Glu Asn Lys Ile
65                  70                  75                 80

Ile Ser Phe Lys Glu Met Asn Pro Pro Asp Asn Ile Lys Asp Thr Lys
            85                  90                 95

Ser Asp Ile Ile Phe Phe Gln Arg Ser Val Pro Gly His Asp Asn Lys
            100                 105                110

Met Gln Phe Glu Ser Ser Ser Tyr Glu Gly Tyr Phe Leu Ala Ser Glu
            115                 120                125

Lys Glu Arg Asp Leu Phe Lys Leu Ile Leu Lys Lys Glu Asp Glu Leu
            130                 135                140

Gly Asp Arg Ser Ile Met Phe Thr Val Gln Asn Glu Asp
145                 150                 155
```

(2) INFORMATION FOR SEQ ID NO: 24:

(i) SEQUENCE CHARACTERISTICS:
        (A) LENGTH: 157 amino acids
        (B) TYPE: amino acid
        (D) TOPOLOGY: linear (ii) MOLECULE TYPE: peptide (xi) SEQUENCE DESCRIPTION: SEQ ID NO: 24:

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
                20                  25                  30

Met Thr Asp Ser Asp Ser Arg Asp Asn Ala Pro Arg Thr Ile Phe Ile
            35                  40                  45

Ile Ser Met Tyr Lys Asp Ser Gln Pro Arg Gly Met Ala Val Thr Ile
        50                  55                  60

Ser Val Lys Ser Glu Lys Ile Ser Thr Leu Ser Ser Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Ser Glu
            115                 120                 125

Lys Glu Arg Asp Leu Phe Lys Leu Ile Leu Lys Lys Glu Asp Glu Leu
        130                 135                 140

Gly Asp Arg Ser Ile Met Phe Thr Val Gln Asn Glu Asp
145                 150                 155
```

(2) INFORMATION FOR SEQ ID NO: 25:

(i) SEQUENCE CHARACTERISTICS:
    (A) LENGTH: 157 amino acids
    (B) TYPE: amino acid
    (D) TOPOLOGY: linear (ii) MOLECULE TYPE: peptide (xi) SEQUENCE DESCRIPTION: SEQ ID NO: 25:

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
                20                  25                  30

Met Thr Asp Ser Asp Ser Arg Asp Asn Ala Pro Arg Thr Ile Phe Ile
            35                  40                  45

Ile Ser Met Tyr Lys Asp Ser Gln Pro Arg Gly Met Ala Val Thr Ile
        50                  55                  60

Ser Val Lys Ser Glu Lys Ile Ser Thr Leu Ser Ala Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
            115                 120                 125

Lys Glu Arg Asp Leu Phe Lys Leu Ile Leu Lys Lys Glu Asp Glu Leu
        130                 135                 140

Gly Asp Arg Ser Ile Met Phe Thr Val Gln Asn Glu Asp
145                 150                 155
```

(2) INFORMATION FOR SEQ ID NO: 26:

```
    (i) SEQUENCE CHARACTERISTICS:
        (A) LENGTH: 157 amino acids
        (B) TYPE: amino acid
        (D) TOPOLOGY: linear (ii) MOLECULE TYPE: peptide (xi) SEQUENCE DESCRIPTION: SEQ ID NO: 26:

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Ser Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Ser Glu Lys Ile Ser Thr Leu Ser Ala Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Ser Glu
            115                 120                 125

Lys Glu Arg Asp Leu Phe Lys Leu Ile Leu Lys Lys Glu Asp Glu Leu
130                 135                 140

Gly Asp Arg Ser Ile Met Phe Thr Val Gln Asn Glu Asp
145                 150                 155

(2) INFORMATION FOR SEQ ID NO: 27:

(i) SEQUENCE CHARACTERISTICS:
        (A) LENGTH: 157 amino acids
        (B) TYPE: amino acid
        (D) TOPOLOGY: linear (ii) MOLECULE TYPE: peptide (xi) SEQUENCE DESCRIPTION: SEQ ID NO: 27:

Asn Phe Gly Arg Leu His Ala Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Ile Gln Ser
                85                  90                  95

Asp Leu Ile Phe Phe Gln Lys Arg Val Pro Gly His Asn Lys Met Glu
            100                 105                 110

Phe Glu Ser Ser Leu Tyr Glu Gly His Phe Leu Ala Cys Gln Lys Glu
            115                 120                 125

Asp Asp Ala Phe Lys Leu Ile Leu Lys Lys Lys Asp Glu Asn Gly Asp
130                 135                 140

Lys Ser Val Met Phe Thr Leu Thr Asn Leu His Gln Ser
```

-continued

```
145                 150                 155
```

(2) INFORMATION FOR SEQ ID NO: 28:

(i) SEQUENCE CHARACTERISTICS:
        (A) LENGTH: 157 amino acids
        (B) TYPE: amino acid
        (D) TOPOLOGY: linear (ii) MOLECULE TYPE: peptide (xi) SEQUENCE DESCRIPTION: SEQ ID NO: 28:

```
Asn Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
            35                  40                  45

Tyr Met Tyr Lys Asp Ser Glu Val Arg Gly Leu Ala Val Thr Leu Ser
        50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Arg Val Pro Gly His Asn Lys Met Glu
            100                 105                 110

Phe Glu Ser Ser Leu Tyr Glu Gly His Phe Leu Ala Ser Gln Lys Glu
        115                 120                 125

Asp Asp Ala Phe Lys Leu Ile Leu Lys Lys Asp Glu Asn Gly Asp
        130                 135                 140

Lys Ser Val Met Phe Thr Leu Thr Asn Leu His Gln Ser
145                 150                 155
```